(12) United States Patent
Iwatani et al.

(10) Patent No.: US 8,510,054 B2
(45) Date of Patent: Aug. 13, 2013

(54) INTRACELLULAR METABOLIC FLUX ANALYSIS METHOD USING SUBSTRATE LABELED WITH ISOTOPE

(75) Inventors: Shintaro Iwatani, Kawasaki (JP); Yoshihiro Usuda, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 275 days.

(21) Appl. No.: 11/048,923

(22) Filed: Feb. 3, 2005

(65) Prior Publication Data

US 2005/0175982 A1 Aug. 11, 2005

(30) Foreign Application Priority Data

Feb. 5, 2004 (JP) ................. 2004-029376

(51) Int. Cl.
*G01N 33/48* (2006.01)
*C12Q 1/00* (2006.01)

(52) U.S. Cl.
USPC .............................................. 702/19; 435/34

(58) Field of Classification Search
USPC .......................................................... 702/19
See application file for complete search history.

(56) References Cited

U.S. PATENT DOCUMENTS 6,764,817 B1 * 7/2004 Schneider ...................... 435/4
2003/0059792 A1 3/2003 Palsson et al.

FOREIGN PATENT DOCUMENTS

| WO | 00/63683 A1 | 10/2000 |
| WO | 2004/011426 A2 | 2/2004 |
| WO | 2005/001736 A2 | 1/2005 |
| WO | 2005/010175 A1 | 2/2005 |

OTHER PUBLICATIONS

Marx et al., "Determination of the Fluxes in the Central Metabolism of *Corynebacterium glutamicum* by Nuclear Magnetic Resonance Spectroscopy Combined with Metabolite Balancing," Biotechnology and Bioengineering, vol. 49 (1996) p. 111-129.*
Christiansen et al., "Metabolic Network Analysis of *Bacillus clausii* on Minimal and Semirich Medium using 13C-Labled Glucose," Metabloic Engineering, vol. 4 (2002) p. 159-169.*
Wittmann et al. "Mass Spectrometry for Metabolic Flux Analysis," Biotechnology and Bioengineering, vol. 62 (6), pp. 739-750 (1999).*
Wiechert, W. et al. "A Universal Framework for $^{13}$C Metabolic Flux Analysis", *Metabolic Engineering*, vol. 3 pp. 265-283, 2001.
Wiechert, W. et al. "Bidirectional Reaction Steps in Metabolic Networks: I. Modeling and Simulation of Carbon Isotope Labeling Experiments", *Biotechnology and Bioengineering*, vol. 55(1) pp. 101-117, 1997.
Wiechert, W. et al. "Bidirectional Reaction Steps in Metabolic Networks: II. Flux Estimation and Statistical Analysis", Biotechnology and Bioengineering, vol. 55(1) pp. 118-135, 1997.
Wiechert, W. et al. "Bidirectional Reaction Steps in Metabolic Networks: III. Explicit Solution and Analysis of Isotopomer Labeling Systems", Biotechnology and Bioengineering, vol. 66(2) pp. 69-85, 1999.
Möllney, M. et al. "Bidirectional Reaction Steps in Metabolic Networks: IV. Optimal Design of Isotopomer Labeling Experiments", Biotechnology and Bioengineering, vol. 66(2) pp. 86-103, 1999.
Petersen, S. et al. "In Vivo Quantification of Parallel and Bidirectional Fluxes in the Anaplerosis of *Corynebacterium glutamicum*", *The Journal of Biological Chemistry*, vol. 275(46) pp. 35932-35941, 2000.
Wittmann, C. et al. "Application of MALDI-TOF MS to lysine-producing *Corynebacterium glutamicum*", Eur. J. Biochem., vol. 268 pp. 2441-2455, 2001.
Wiechert, W. "Modeling and simulation: tools for metabolic engineering", *Journal of Biotechnology*, vol. 94 pp. 37-63, 2002.
Wiechert, W. "Minireview—$^{13}$C Metabolic Flux Analysis", *Metabolic Engineering*, vol. 3 pp. 195-206, 2001.
XP-002329350: Al Zaid Siddiquee, K., et al., "Metabolic flux analysis of *pykF* gene knockout *Escherichia coli* based on $^{13}$C-labeling experiments together with measurements of enzyme activities and intracellular metabolite concentrations", *Applied Microbiology and Biotechnology*, vol. 63, No. 4, pp. 407-417, (2004).
XP-002329346: Hellerstein, M.K., "New stable isotope-mass spectrometric techniques for measuring fluxes through intact metabolic pathways in mammalian systems: introduction of moving pictures into functional genomics and biochemical phenotyping", *Metabolic Engineering*, vol. 6, No. 1, pp. 85-100, (2004).
XP-002329347: Puccetti, C., et al., "$^{13}$C-NMR isotopomer distribution analysis: a method for measuring metabolic fluxes in condensation biosynthesis", *NMR in Biomedicine*, vol. 15, No. 6, pp. 404-415, (2002).
XP-002329348: Shimizu, A., "A Review on Metabolic Pathway Analysis with Emphasis on Isotope Labeling Approach", *Biotechnology and Bioprocess Engineering*, vol. 7, No. 5, pp. 237-251, (2002).
XP-002329349: Forbes, N.S., et al., "Using Isotopomer Path Tracing to Quantify Metabolic Fluxes in Pathway Models Containing Reversible Reactions", *Biotechnology and Bioengineering*, vol. 74, No. 3, pp. 196-211, (2001).
XP-002329353: Möllney, M., W. Weichert, et al., "Bidirectional Reaction Steps in Metabolic Networks: IV. Optimal Design of Isotopomer Labeling Experiments", *Biotechnology and Bioengineering*, vol. 66, No. 2, pp. 86-103, (1999).
XP-002329357: Schmidt, K., et al., "Quantification of Intracellular Metabolic Fluxes from Fractional Enrichment and $^{13}$C-$^{13}$C Coupling Constraints on the Isotopomer Distribution in Labeled Biomass Components", *Metabolic Engineering*, vol. 1, No. 2, pp. 166-179, (1999).

(Continued)

*Primary Examiner* — Anna Skibinsky
(74) *Attorney, Agent, or Firm* — Nath, Goldberg & Meyer; Jerald L. Meyer; Sanjana Mangalagiri

(57) ABSTRACT

A method for intracellular metabolic flux analysis comprising (a) culturing cells in a medium not containing any isotope-labeled substrate to a target phase of the metabolic flux analysis, (b) adding an isotope-labeled substrate to the medium, and continuing culture and collecting samples from the medium in time course, (c) measuring isotope distribution in an intracellular metabolite contained in the samples collected in time course, (d) performing a regression analysis for measured data and calculating an isotope distribution ratio in a steady state, and (e) analyzing a metabolic flux of the cultured cells by using the calculated isotope distribution ratio.

11 Claims, 8 Drawing Sheets

(56) References Cited

OTHER PUBLICATIONS

XP-002329356: Wittmann, C., et al., "Mass Spectrometry for Metabolic Flux Analysis", *Biotechnology and Bioengineering*, vol. 62, No. 6, pp. 739-750, (1999).

Nöh, et al., "Metabolic flux analysis at ultra short time scale: Isotopically non-stationary 13C labeling experiments", Journal of Biotechnology, vol. 129, pp. 249-267, (2007).

Wahl, et al., "13C labeling experiments at metabolic nonstationary conditions: An exploratory study", BMC Bioinformatics, vol. 9, pp. 152-169 (pp. 1 through 18), (2008).

XP-002329354: Wittmann, C., et al., "Application of MALDI-TOF MS to lysine-producing *Corynebacterium glutamicum*", *Eur. J. Biochemistry*, vol. 268, pp. 2441-2455, (2001).

XP-002329355: Wittmann, C., et al., "Modeling and Experimental Design for Metabolic Flux Analysis of Lysine-Producing *Corynebacteria* by Mass Spectrometry", *Metabolic Engineering*, vol. 3, pp. 173-191, (2001).

XP-002329353: Möllney, M., W. Wiechert et al., "Bidirectional Reaction Steps in Metabolic Networks: IV. Optimal Design of Isotopomer Labeling Experiments", *Biotechnology and Bioengineering*, vol. 66, No. 2, pp. 86-103, (1999).

XP-002329352: Wiechert, W., et al., "Bidirectional Reaction Steps in Metabolic Networks: III. Explicit Solution and Analysis of Isotopomer Labeling Systems", *Biotechnology and Bioengineering*, vol. 66, No. 2, pp. 69-85, (1999).

XP-004179663: Schmidt, K., et al., "Quantitative analysis of metabolic fluxes in *Escherichia coli*, using two-dimensional NMR spectroscopy and complete isotopomer models", *Journal of Biotechnology*, vol. 71, No. 1-3, pp. 175-189, (1999).

XP-002329357: Schmidt K., et al., "Quantification of Intracellular Metabolic Fluxes from Fractional Enrichment and $^{13}$C-$^{13}$C Coupling Constraints on the Isotopomer Distribution in Labeled Biomass Components", *Metabolic Engineering*, vol. 1, No. 2, pp. 166-179, (1999).

XP-002329356: Wittmann, C., et al., "Mass Spectrometry for Metabolic Flux Analysis", *Biotechnology and Bioengineering*, vol. 62, No. 6, pp. 739-750. (1999).

XP-002329351: Wiechert, W., et al., "Bidirectional Reaction Steps in Metabolic Networks: II. Flux Estimation and Statistical Analysis", *Biotechnology and Bioengineering*, vol. 55, No. 1, pp. 118-135, (1997).

\* cited by examiner

INTRACELLULAR METABOLIC FLUX ANALYSIS METHOD USING SUBSTRATE LABELED WITH ISOTOPE

BACKGROUND OF THE INVENTION

The present invention relates to a method for analyzing a metabolic flux, that is, a metabolic flux analysis method, a program for the method and a recording medium recording the program. Specifically, the present invention relates to a metabolic flux analysis method using an isotope-labeled substance, a program for the method and a recording medium recording the program.

The metabolic flux analysis method is a method for quantitatively determining an intracellular metabolic flux by analyzing intracellular balances of metabolites or isotope-labeled compounds and conducting isotope compound tracer experiments with an analytical technique such as nuclear magnetic resonance (NMR) or mass spectrometry (MS). In recent years, this method has drawn attentions as a technique for stoichiometrically analyzing the quantitative ratio of metabolites (carbon balance) in metabolic pathways in an objective cell (Metabolic Engineering 3, 265-283, 2001).

Various studies are being conducted to develop an accurate analytical technique for use in metabolic flux analyses. The theory concerning metabolic flux analysis using isotope-labeled substrates has been reported in many papers and is being established (Biotechnology and Bioengineering 55, 101-117, 1997. Biotechnology and Bioengineering 55, 118-13, 1997% Biotechnology and Bioengineering 66, 69-85, 1999% Biotechnology and Bioengineering 66, 86-103, 1999). Although many experiments are being conducted to establish a metabolic flux analysis method, researches based on a continuous culture method utilizing a synthetic medium as an ideal condition are common to obtain high analytical precision (Journal of Biological Chemistry 275, 35932-35941, 2000). Further, although there are a few reports on metabolic flux analysis performed by batch culture as a more practical culture method, only isotope distributions of several substances discharged in a medium have been measured, and no calculation has been performed at all based on the measurement of isotope distributions in intracellular substances (European Journal of Biochemistry 268, 2441-2455, 2001). Isotope substrates are generally expensive and when an experiment is conducted according to the conventional method, the considerably increasing costs of the experiment become a problem (Journal of Biotechnology 94, 37-63, 2002% Metabolic Engineering 3, 195-205, 2001).

SUMMARY OF THE INVENTION

The conventional metabolic flux analyses performed by using an isotope-labeled compound have a drawback that they use a large amount of the isotope-labeled compound as a substrate and therefore require extremely high cost, and have a problem that although they are suitable for analysis of culture of which whole system is in a steady state like, mainly, continuous culture, they are not suitable for batch culture or fed-batch culture. In practical researches and developments as well as actual productions, a more inexpensive metabolic flux analysis technique usable at any culture phase and for any type of culture method is desired.

The inventors of the present invention assiduously studied in view of the aforementioned problems, and as a result, they found, for a metabolic flux analysis performed by using an isotope-labeled compound, a method for calculating an isotope distribution ratio of the isotope-labeled compound required for the metabolic flux analysis by using a small amount of the isotope-labeled compound. That is, they found that by analyzing the time course of metabolites of cells cultured to a target phase of the metabolic flux analysis and then cultured in a medium to which a small amount of an isotope-labeled substrate is added as a carbon source to provide measured values and performing a particular regression analysis for the obtained measured values, an isotope distribution ratio of the isotope-labeled compound could be calculated for the target phase of the metabolic flux analysis.

The present invention was accomplished based on the aforementioned finding and provides the followings.

(1) A method for intracellular metabolic flux analysis comprising the following steps:
(a) culturing cells in a medium not containing any isotope-labeled substrate to a target phase of the metabolic flux analysis,
(b) adding an isotope-labeled substrate to the medium, and continuing culture and collecting samples from the medium in time course,
(c) measuring isotope distribution in an intracellular metabolite contained in the samples collected in time course,
(d) performing a regression analysis for measured data and calculating an isotope distribution ratio in a steady state, and
(e) analyzing a metabolic flux of the cultured cells by using the calculated isotope distribution ratio.

(2) The method according to (1), wherein the substrate is added in such an amount that all of the substrate is not consumed during a period of collecting the samples.

(3) The method according to (1) or (2), wherein the regression analysis is performed by using a specific function represented by the following equation (I):

$$MDV(M_i)_\xi = \{(a*t^\lambda + b)/d + c*t^\lambda)\}^\eta \quad (I)$$

wherein $MDV(M_i)_\xi$ is a mass distribution vector of a substance $\xi$, $\eta$ is an integer of 1 or larger, $\lambda$ is a positive number, t is time, and a, b, c and d are constants.

(4) The method according to any one of (1) to (3), wherein the metabolic flux analysis is performed by a method comprising execution of an optimization algorithm.

(5) The method according to (4), wherein the optimization algorithm is an evolutionary algorithm.

(6) The method according to any one of (1) to (5), wherein the metabolic flux analysis is performed by a method utilizing an intracellular metabolic flux model constructed for an intracellular metabolic flux to be analyzed, and a function representing the intracellular metabolic flux model contains an exchange coefficient of a cell-constituting substance and the same substance in an intracellular pool.

(7) The method according to any one of (1) to (5), wherein the cells are those of a microorganism having an ability to produce a useful compound.

(8) The method according to (7), wherein the useful compound is at least one of an amino acid and an organic acid.

(9) The method according to any one of (1) to (8), wherein culture of the cells is batch culture or fed-batch culture.

(10) The method according to any one of (1) to (9), wherein the intracellular metabolite is at least one of an amino acid and an organic acid, or a major metabolic intermediate thereof, or both.

(11) The method according to any one of (1) to (10), wherein the isotope distribution is measured by mass spectrometry.

(12) A program used for a method for intracellular metabolic flux analysis, which causes a computer to function as:
(I) a means for storing data of isotope distribution measured by the following steps (a) to (c):

(a) culturing cells in a medium not containing any isotope-labeled substrate to a target phase of the metabolic flux analysis, (b) adding an isotope-labeled substrate to the medium, and continuing culture and collecting samples from the medium in time course, and (c) measuring isotope distribution in a intracellular metabolite contained in the samples collected in time course, (II) a means for performing a regression analysis for stored data to calculate an isotope distribution ratio in a steady state, and (III) a means for analyzing a metabolic flux of the cultured cells by using the calculated isotope distribution ratio.

(13) A computer-readable recording medium, which records the program as defined in (12).

The method of the present invention uses a small amount of an isotope-labeled compound substrate, and therefore it enables metabolic flux analysis at a low cost. Moreover, it enables calculation of a metabolic flux by analysis of dynamic change in isotope distribution in a short time, and therefore it is also effective for analysis of culture in an unsteady state in batch culture, fed-batch culture etc.

BRIEF EXPLANATION OF DRAWINGS

FIG. 1-2 shows result of regression analysis (at 25 hours after the start of cultivation; pulse addition of isotope-labeled substrate).

FIG. 2 shows results of metabolic flux analysis (at 17 hours after the start of cultivation; initial addition of isotope-labeled substrate).

DETAILED DESCRIPTION OF THE INVENTION

Figure 1:
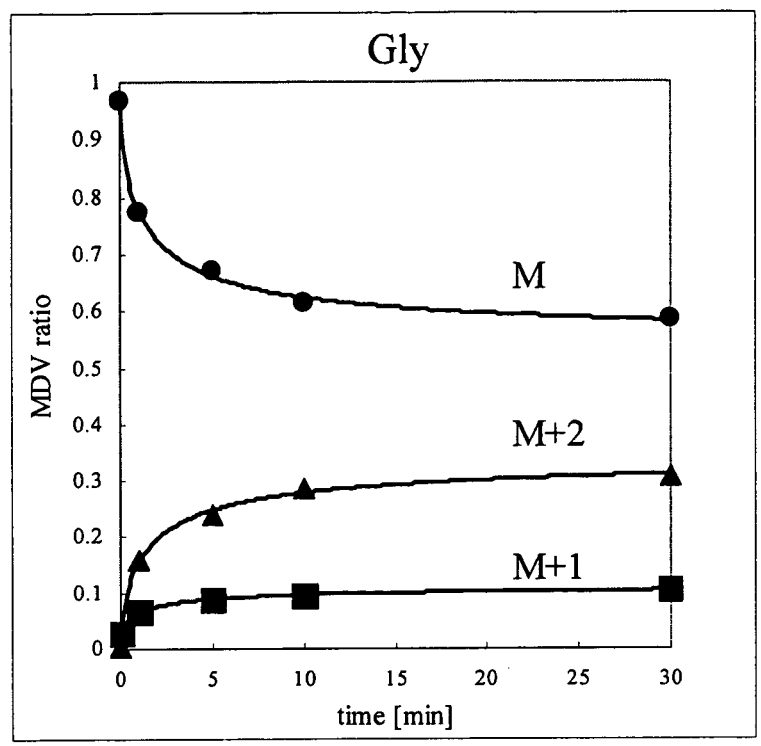
FIG. 1-1 shows results of regression analysis (at 17 hours after the start of cultivation; pulse addition of isotope-labeled substrate).
Figure 1:
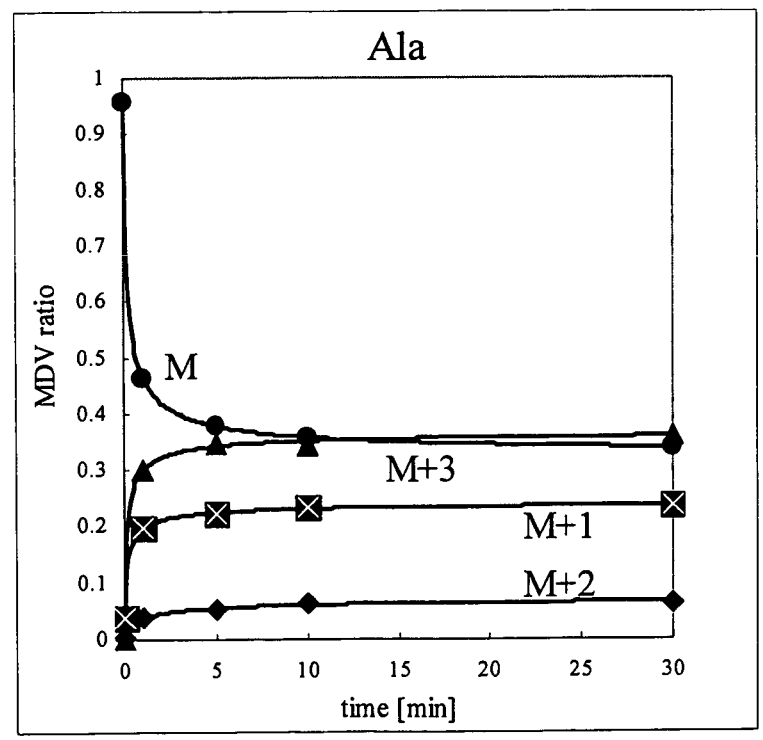
Figure 1:
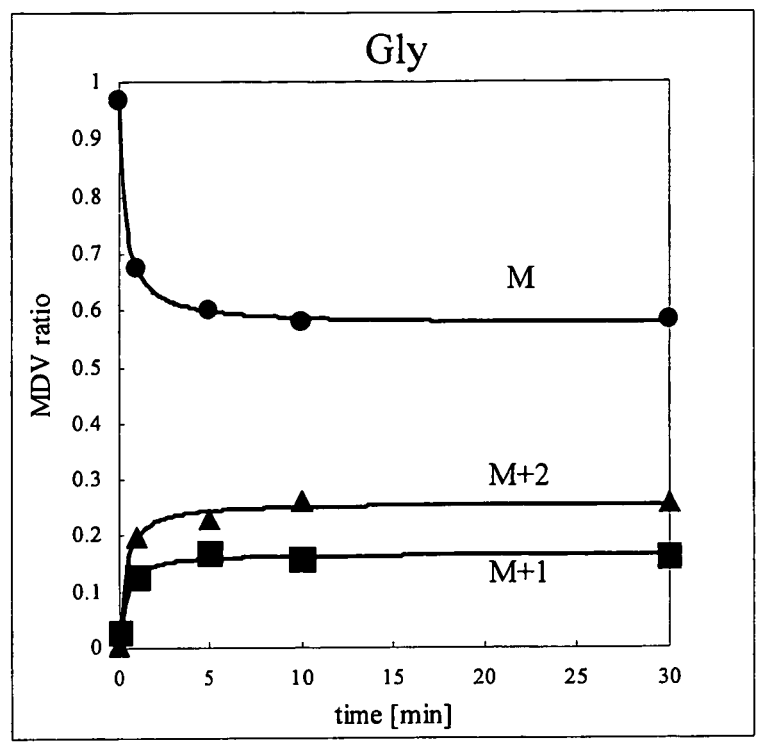
Figure 2:
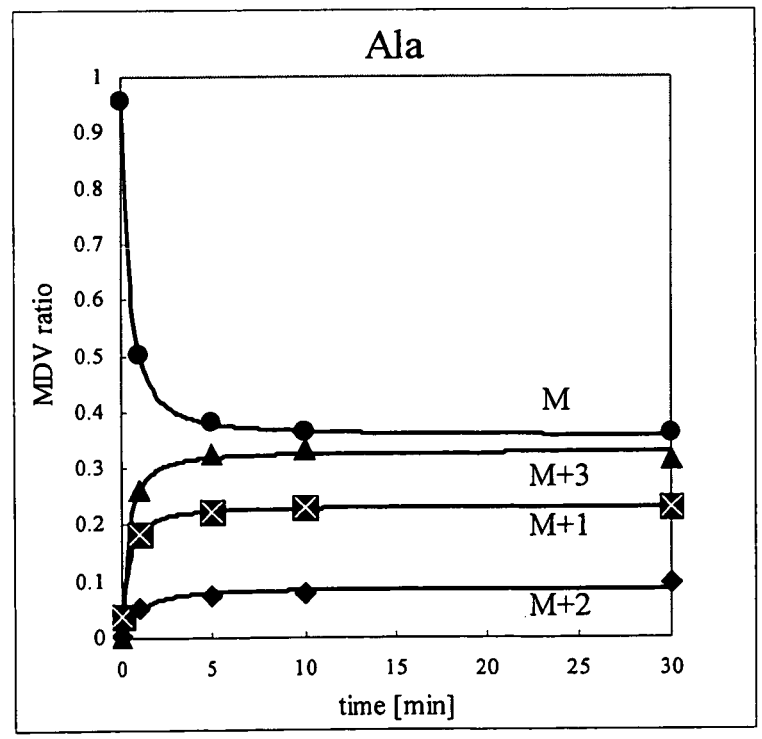
Figure 2:
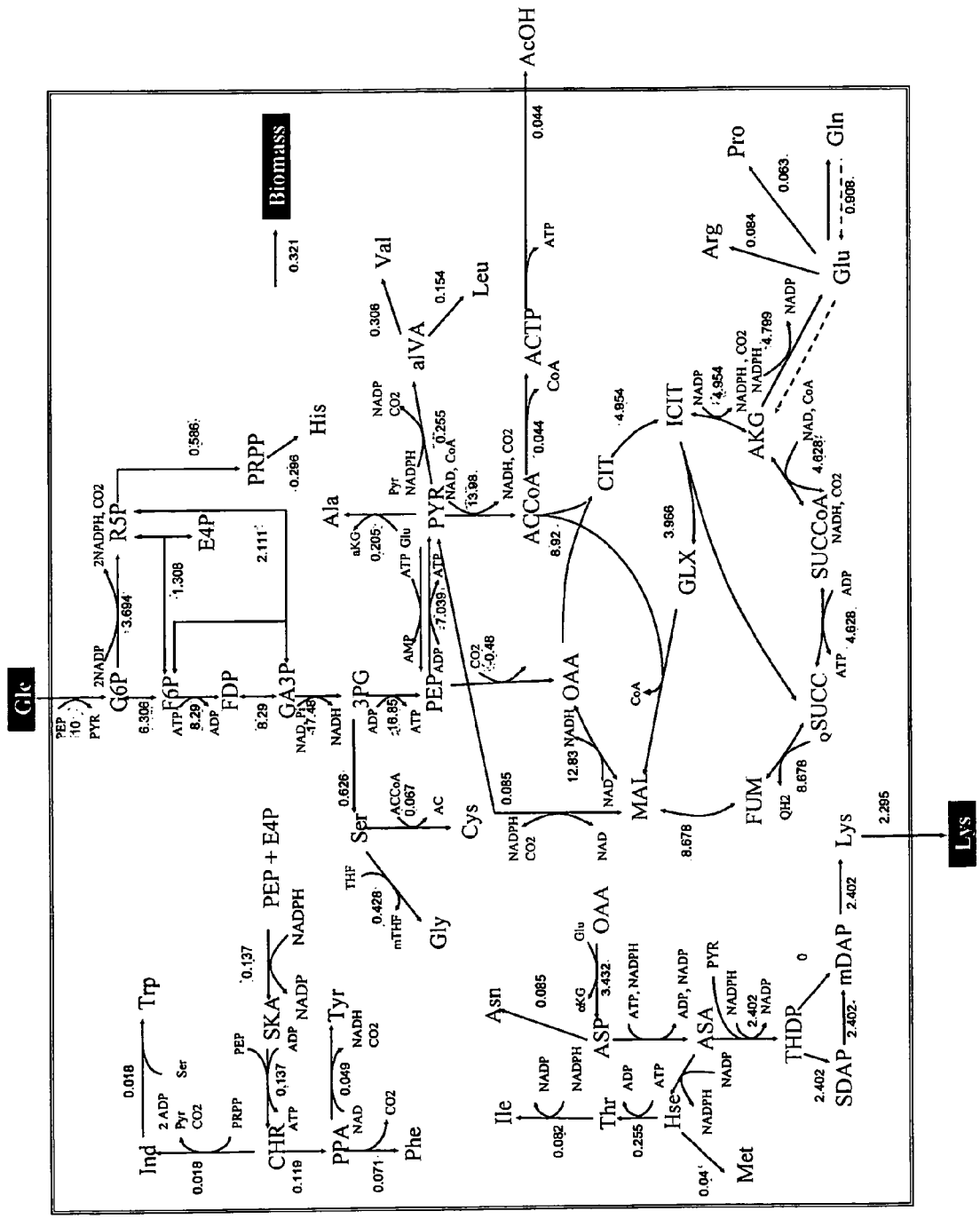
Figure 3:
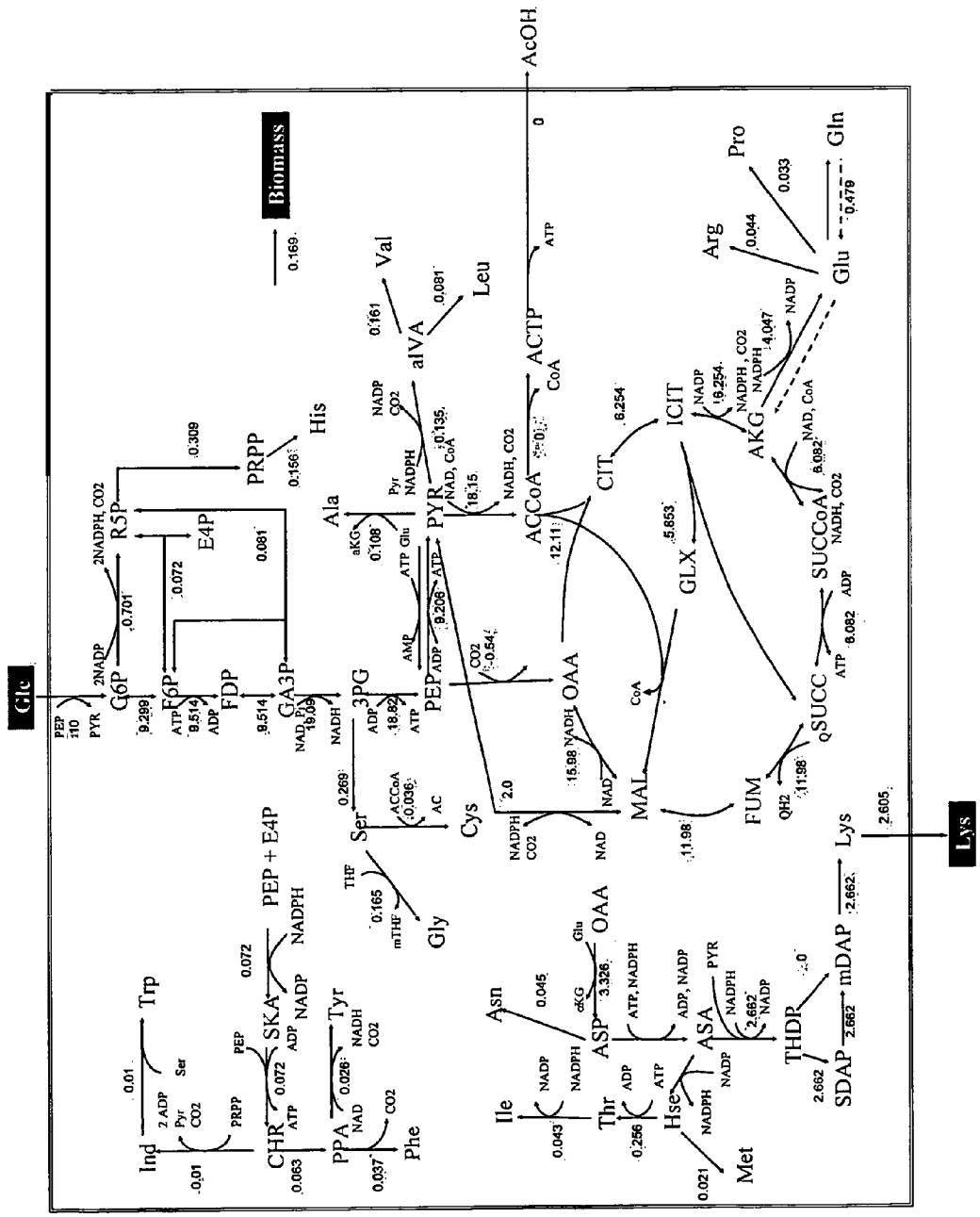
FIG. 3 shows results of metabolic flux analysis (at 25 hours after the start of cultivation; initial addition of isotope-labeled substrate).
Figure 4:
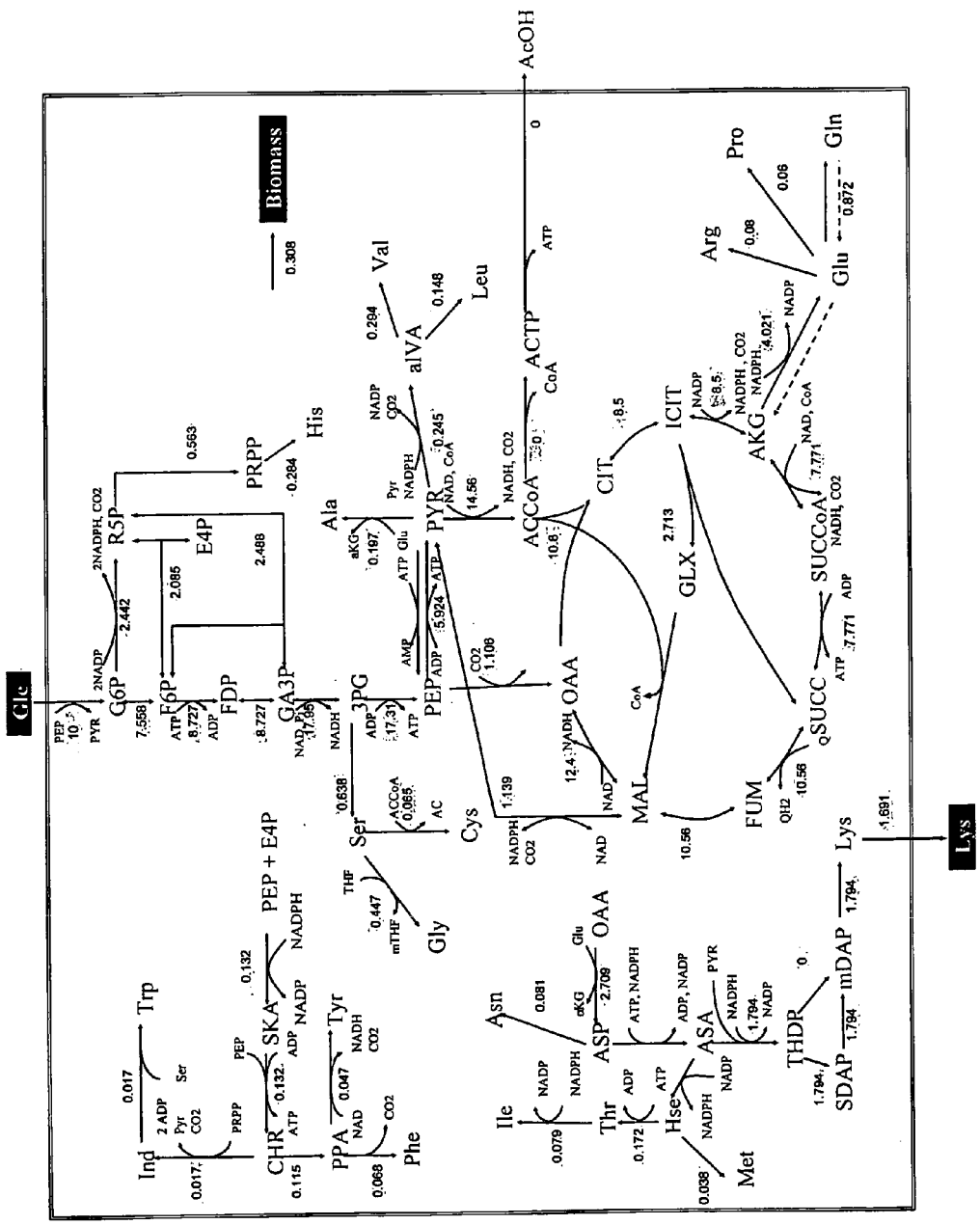
FIG. 4 shows results of metabolic flux analysis (at 17 hours after the start of cultivation; pulse addition of isotope-labeled substrate).
Figure 5:
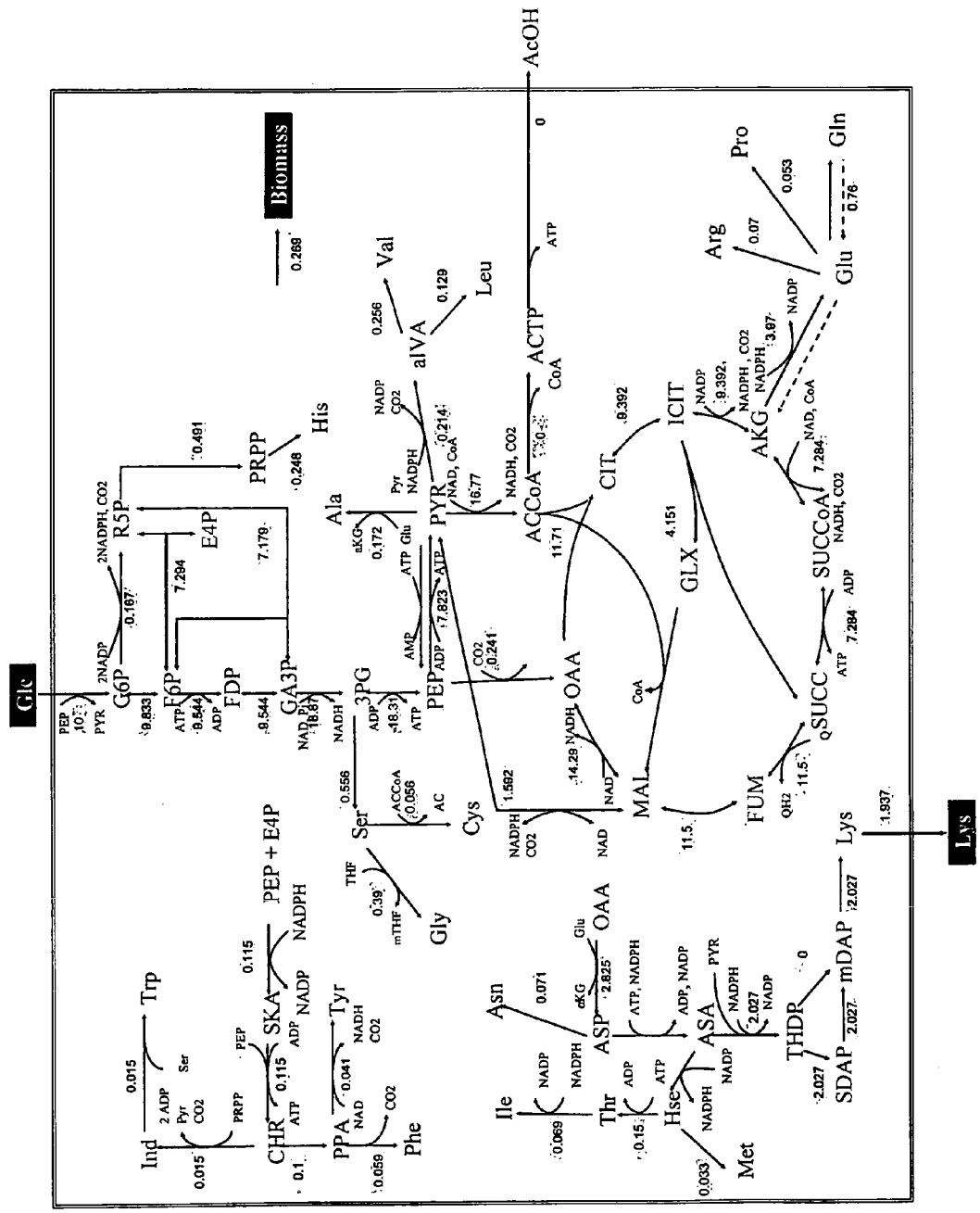
FIG. 5 shows results of metabolic flux analysis (at 25 hours after the start of cultivation; pulse addition of isotope-labeled substrate).

Hereafter, the present invention will be explained in detail.

The intracellular metabolic flux referred to in the present invention is a flux of an intracellular metabolite derived from a stoichiometric model of an intracellular chemical reaction and the law of mass action between metabolites.

Any kinds of cell can be subject to analysis in the present invention, and examples thereof include, in particular, cells used for production of a substance, such as various cultured cells, fungi, yeasts and various bacteria. They are preferably microorganisms having an ability to produce useful compounds, for example, amino acids, nucleic acids or organic acids. Preferred examples of the microorganisms having an ability to produce amino acids, nucleic acids or organic acids include *Escherichia coli, Bacillus* bacteria, coryneform bacteria and so forth.

Hereafter, the steps (a) to (e) will be explained one by one.

The step (a) is a step of culturing cells in a medium not containing any isotope-labeled substrate to a target phase of the metabolic flux analysis. The target phase of the metabolic flux analysis is a state that intracellular metabolism is not stopped. Any phases during culture including a steady state and an unsteady state in batch culture, fed-batch culture etc. may be the target phase. Among these, fed-batch culture is a particularly preferred object.

The isotope in the isotope-labeled substrate is the isotope used in the step (b). The isotope-labeled substrate means a substance that can be distinguished from the corresponding naturally occurring substance by the isotope, i.e., a substance containing the isotope at a ratio different from the ratio of the isotope existing in the corresponding naturally occurring substance. Therefore, the medium not containing any isotope-labeled substrate means, when the medium contains the same substrate as the substrate added in the step (b) before the addition, a medium containing only the substrate containing the isotope at the same ratio as the naturally occurring ratio of the isotope in the substrate.

The medium and culture conditions are suitably chosen depending on the cells to be cultured and the target phase of metabolic flux analysis. Examples of the medium used include, for example, ordinary media containing a carbon source, nitrogen source, inorganic ions and other organic trace nutrient sources as required. As the carbon source, sugars such as glucose, lactose, galactose, fructose and starch hydrolysate, alcohols such as glycerol and sorbitol, organic acids such as fumaric acid, citric acid and succinic acid and so forth can be used. As the nitrogen source, inorganic ammonium salts such as ammonium sulfate, ammonium chloride and ammonium phosphate, organic nitrogen such as soybean hydrolysate, ammonia gas, aqueous ammonia and so forth can be used. As the inorganic ions or source thereof, potassium phosphate, magnesium sulfate, iron ions, manganese ions and so forth are added in a small amount. Other than these, as organic trace nutrient sources, appropriate amounts of vitamin $B_1$, yeast extract and so forth are desirably added. The culture is usually performed under an aerobic condition. The culture temperature is usually controlled to be 25 to 45° C., and pH is usually controlled to be 5 to 9 during the culture. Inorganic or organic acidic or alkaline substances such as ammonia gas can be used for pH adjustment. By using such media, cells can be cultured to a target phase of the metabolic flux analysis.

The step (b) is a step of adding an isotope-labeled substrate to the medium of the step (a), and continuing culture and collecting samples from the medium in time course.

This step is performed when the target phase of the metabolic flux analysis is attained by the culture of the step (a). The samples may be collected from the culture broth in an amount required to measure isotope distribution in the step (c). When the analysis is performed by using mass spectrometry, an amount of about 100 mg per sample in terms of cell weight may be usually sufficient, and the amount is adjusted depending on the number of compounds to be analyzed.

Although the isotope used in the present invention is usually a stable isotope, a radioactive isotope can also be used for the same purpose. Examples of isotope-labeled substrates include isotope-labeled glucose, sucrose, fructose, acetic acid, various amino acids and so forth. When the isotope-labeled substrate is used as a carbon source, examples of the substrate include glucose of which carbon at 1-position is labeled with a stable isotope and/or glucose all of which carbons are labeled with a stable isotope. Examples of the isotope include $^{13}C$, $^{14}C$, $^{17}O$, $^{18}O$, $^{15}N$, $^{32}P$, $^{33}P$, $^{33}S$, $^{34}S$, $^{35}S$, $^{36}$S, $^{2}$H, $^{3}$H and so forth. When a carbon source such as glucose is used as the substrate, use of $^{13}$C or $^{18}$O is preferred.

The isotope used for the labeling and labeling pattern are suitably chosen according to the analysis method used in the step (e). When an analysis model is used as the metabolic flux analysis method, it is preferable to perform sensitivity analysis of the analysis model and thereby determine requirements for the isotope-labeled substrate (labeling position, mixing ratio of substrates labeled at different positions etc.). Examples of the method of the sensitivity analysis include the method described by Mollney, M., W. Wiechert, D. Kowanatzki, and A. A. de Graaf., Biotechnology and Bioengineering 66, pp. 86-103. However, so long as the method allows analysis of requirements for substrate, it is not particularly limited to the method mentioned above.

The amount of the isotope-labeled substrate to be added may be such an amount that data sufficient for performing a regression analysis in the step (d) can be measured in the step (c). The amount is preferably such an amount that all of the substrate should not be decomposed during collection of the samples.

When the isotope-labeled substrate is added, the substrate in the medium is preferably decreased to an amount substantially corresponding to depletion of the substrate so that the ratio of the isotope-labeled substrate should become high (for example, 90 mol % or more). In the case of culture in which a substrate is added during culture as in fed-batch culture, the amount of the substrate can be decreased by terminating addition of the substrate.

If the substrate is depleted, state of cells changes, and metabolic flux analysis for a target phase becomes impossible. Therefore, it is preferable to directly or indirectly monitor the amount of the substrate. For example, if the substrate is depleted, dissolved oxygen concentration in the medium increases. Therefore, by monitoring change of dissolved oxygen concentration, the point immediately before depletion can be determined.

Time and number of collection of samples can be selected so that reliable values can be calculated in the regression analysis in the step (d). Although they can be selected depending on the type of substrate added, method of the regression analysis, culture conditions etc., samples can usually be collected, for example, 3 to 5 times during a period of 0 to 60 minutes after the addition. Further, collection intervals immediately after the addition are preferably shorter than subsequent collection intervals.

The step (c) is a step of measuring isotope distribution in an intracellular metabolite contained in the samples collected in time course in the step (b).

The intracellular metabolites referred to in the present invention are products or intermediates metabolized in a cell. Many findings about intracellular metabolites as well as the biochemical reactions thereof have been obtained and accumulated in databases, for example, Kyoto Encyclopedia of Genes and Genomes.

Examples of isotope distribution include isotopomer distribution vectors (Biotechnology and Bioengineering, 55, pp. 831-840), mass distribution vectors (Biotechnology and Bioengineering, 62, pp. 739-750) and so forth. Mass distribution vectors are preferred, because they can be measured by mass spectrometry. Examples of the measurement method include mass spectrometry such as high-performance liquid chromatography mass spectrometry (LC-MS), gas chromatography mass spectrometry (GC-MS), nuclear magnetic resonance spectrum (NMR) and so forth, and mass spectrometry is particularly preferred.

Isotope distribution in an intracellular metabolite contained in samples can be measured by a usual method. For example, for mass distribution vector, a method of extracting an intracellular metabolite from samples and analyzing the extract by mass spectrometry. Examples of the method for extracting an intracellular metabolite from a sample include usually used methods such as disruption by ultrasonication and extraction of intracellular substances with acid.

In the measurement, it is preferable to correct influences of naturally occurring isotopes. Examples of correction method include the method of Wittmann and Heinzle (Biotechnology and Bioengineering, 62, pp. 739-750). However, so long as a method enabling correction of analysis data by utilizing an existing ratio of naturally occurring isotope is chosen, the method is not limited to the aforementioned method.

The step (d) is a step of performing a regression analysis for the data measured in the step (c) to calculate an isotope distribution ratio in steady state.

The method of regression analysis is not particularly limited, so long as a method that can calculate isotope distribution ratio in steady state is chosen, and examples include nonlinear regression analysis and so forth. A regression analysis using a specific function represented by the equation (I) is preferred. In the regression analysis using this specific function, the constants a, b, c and d are obtained by regression from the measured data, and an isotope distribution ratio is calculated in accordance with the equation (I) of which constants are determined while defining t as infinite, as an isotope distribution ratio of a steady state. In the equation (I), η and λ are chosen so that the regression error for the measured data should become minimum. t represents time lapsed before each measurement, and when the time of addition of the isotope-labeled substrate is considered as zero.

The step (e) is a step of analyzing a metabolic flux in the cultured cells by using the isotope distribution ratio calculated in the step (d).

Although the step (e) is not particularly limited so long as it is a step of analyzing a metabolic flux in cultured cells by using an isotope distribution ratio, it is usually performed by a method of analyzing an intracellular metabolic flux from analytical values of cells cultured in a medium containing a substrate containing an isotope-labeled carbon atom, nitrogen atom, oxygen atom, hydrogen atom, phosphorus atom, sulfur atom or the like, based on an intracellular metabolic flux model constructed for the intracellular metabolic flux to be analyzed.

The intracellular metabolic flux model is not particularly limited so long as it is constructed for a metabolic flux to be analyzed, and it may be an intracellular metabolic flux model constructed by using a usual construction method. The expression "constructed for a metabolic flux" means that a reaction (reaction route) of the metabolic flux to be analyzed is included in the constructed intracellular metabolic flux model.

Examples of the construction method of intracellular metabolic flux model for a metabolic flux include the methods described in Metabolic Engineering, 3, pp. 265-283, 2001; Wiechert, W. and de Graaf, A. A. Biotechnology and Bioengineering, 55, pp. 101-117, 1997; Metabolic Engineering, 3, pp. 195-205, 2001; Metabolic Engineering, 3, pp. 173-191, 2001; Biotechnology and Bioengineering, 55, pp. 831-840, 1997 and so forth.

Although any reaction route may be used as the reaction route for which a metabolic flux is analyzed so long as a major intracellular metabolic route is selected, glycolysis, TCA cycle, pentose phosphate cycle and synthesis routes peculiar to various amino acids are preferably included, because they are important in view of the practical usefulness of production of useful compounds by microbial fermentation.

In the construction of an intracellular metabolic flux model, a reaction route may be simplified. For example, a series of reactions with no branching of the route may be considered as one reaction, and metabolites before and after a metabolic reaction with high rate, one of which is converted into the other by the reaction, may be considered as one metabolite.

The analytical values of cells are measurable values of cells cultured in a medium containing a substrate labeled with an isotope as a carbon source, and examples include, for example, analytical values of isotope distribution in a metabolite, cell production rate, useful substance production rate and so forth. The analytical values of isotope distributions are not particularly limited so long as they reflect the isotope distributions, and examples thereof include isotopomer distribution vectors (Biotechnology and Bioengineering, 55, pp. 831-840), mass distribution vectors (Biotechnology and Bioengineering, 62, pp. 739-750) and so forth. Mass distribution vectors are preferred, because they can be measured by mass spectrometry.

The step of determining an intracellular metabolic flux from analytical values of cells cultured in a medium containing an isotope-labeled substrate as a carbon source can be performed according to a usual determination method. When the analytical values include analytical values of isotope distributions, the determination is usually made by using an isotopomer balance equation (refer to, for example, Biotechnology and Bioengineering, 66, pp. 69-85, 1999).

When the analytical values of cells are sufficient to calculate variables in a metabolic flux model (when the metabolic flux model is represented by a stoichiometric matrix, sufficient to obtain a solution), variables in the metabolic flux model are determined based on the analytical values of cells, and thereby the metabolic flux can be determined. When the analytical values of cells are not sufficient to calculate variables in the metabolic flux model, a part of other isotope distribution variables in the metabolic flux model are usually considered as free variables. Then, based on using the free variables, the analytical values of cells other than the isotope distribution and the labeling pattern in the used substrate (positions and number of isotopes, and proportions of substrates when two or more kinds of substrates having different number of isotopes at different positions are used), isotope distributions are calculated. The flux optimization can be performed by comparison between values of isotope distribution calculated from the metabolic flux model and analytical values of the isotope distribution to determine variables in the metabolic flux model. Thus, the metabolic flux can be determined. Examples of such an optimization method include the methods described in Metabolic Engineering, 3, pp. 265-283, 2001; Biotechnology and Bioengineering, 55, pp. 118-135, 1997; Biotechnology and Bioengineering, 66, pp. 69-85, 1999 and so forth.

In the step of determining an intracellular metabolic flux from the analytical value of the isotope distribution in a metabolite in cells cultured in a medium containing an isotope-labeled substrate as a carbon source, the labeling pattern of the substrate can be determined by a usual method (refer to, for example, Biotechnology and Bioengineering, 66, pp. 86-103, 1999).

The method for analyzing an intracellular metabolic flux from analytical values of cells cultured in a medium containing an isotope-labeled substrate as a carbon source based on an intracellular metabolic flux model constructed for the intracellular metabolic flux to be analyzed, preferably satisfies at least one of the following conditions (e-a) to (e-c).

(e-a) The analytical values of cells include an analytical value of isotope distribution in an intracellular metabolite included in the intracellular metabolic flux model, and the analytical value of isotope distribution in the intracellular metabolite is corrected for a degree of synthesis and degradation between the intracellular metabolite and a cell component produced by integration of the intracellular metabolite.

(e-b) The intracellular metabolic flux model includes a useful compound and/or a major metabolic intermediate thereof; the analytical values of cells include an uptake rate of a compound in a medium into cells, which compound is identical to the intracellular metabolite and unlabeled with an isotope, and an analytical value or values of isotope distribution in the useful compound and/or the major metabolic intermediate thereof; and the analytical value or values of isotope distribution in the useful compound and/or the major metabolic intermediate thereof are corrected for influence of a rate of inflow into a metabolic pathway on the isotope distribution in the useful compound and/or the major metabolic intermediate thereof on the assumption that a rate obtained by subtracting a rate of integration into a cell component from the uptake rate is the rate of inflow into the metabolic pathway.

(e-c) The intracellular metabolic flux model includes a carbon dioxide fixation reaction and a carbon dioxide production reaction, and carbon dioxide used in the fixation reaction is assumed as carbon dioxide produced in the production reaction.

The cell component referred to in the preferred embodiment is a substance constituting a cell, which is produced by integration of the intracellular metabolite. Examples thereof include substances such as proteins, carbohydrates, nucleic acids and lipids. Further, a degradation product of the cell component means a degradation product at the same level of the intracellular metabolites integrated into the cell component. For example, when the cell component is a protein produced by integration of amino acids, the degradation products are amino acids. In the present specification, when the cell component is a protein produced by integration of amino acids, in particular, it is also referred to as a cellular protein. Further, amino acids as a degradation product of a cellular protein are also referred to as cellular protein-hydrolyzed amino acids.

Each condition will be explained below.

According to the condition (e-a), in calculation of the metabolic flux, the isotope distribution in the intracellular metabolite (e.g. amino acid) is corrected in consideration of the influence of an intracellular metabolite produced by degradation of an intracellular component (e.g. cellular protein) produced in the cell growth phase, that is, an exchange reaction between intracellular metabolite pool and intracellular metabolites produced by degradation of the intracellular component. As for the correction method, the analytical value of the isotope distribution in the intracellular metabolite may be corrected based on the exchange reaction, or the exchange reaction may be included in the intracellular metabolic flux model. When the exchange reaction is included in the intracellular metabolic flux model, the intracellular metabolic flux model includes the exchange reaction between the intracellular metabolite and the cell component produced by integration of the intracellular metabolite, and the analytical values of cells include the analytical value of the isotope distribution in the intracellular metabolite and an analytical value of isotope distribution in the degradation product of cell component. When the exchange reaction is included in the intracellular metabolic flux model, a corrected analytical value of the isotope distribution in the intracellular metabolite is not directly used. However, by determining the intracellular metabolic flux based on the metabolic flux model, the analytical value of the isotope distribution in intracellular metabolite is become to be corrected as a result. An exchange reaction may be represented by an exchange reaction coefficient of a substance in a cell constituent and the substance in intracellular pools (for example, a protein degradation coefficient, Pex). When calculation is made by setting the exchange reaction coefficient independently with respect to each substance, it is expected that accuracy of analysis increases.

Specific examples of the method for correcting isotope distribution in an intracellular metabolite include a method of constructing the intracellular metabolic flux model to include an exchange reaction between the intracellular metabolite and the cell component produced by integration of the intracellular metabolite so that the analytical values of the isotope distributions in the intracellular metabolite and the degradation product of the cell component are included in the analytical values of cells.

Another example of the correction method is a method comprising 1) the step of measuring isotope distribution in the intracellular metabolite and isotope distribution in a degradation product of the cell component, and 2) the step of optimizing the degree of synthesis and degradation between the intracellular metabolite and the cell component based on the results obtained in the step 1) by an optimization algorithm. In this embodiment, the degree of synthesis and degradation is preferably expressed by using a variable defined with an exchange reaction coefficient. Further, examples of the optimization method include the evolutionary algorithm (Journal of Theoretical Biology, 199, pp. 45-61, 1999) and other methods, and the evolutionary algorithm is preferred. In this embodiment, it is preferred that the intracellular metabolite is an amino acid and/or an organic acid, and that the cell component is a protein.

In an embodiment using the analytical value of isotope distribution in the degradation product of the cell component, the analytical value of isotope distribution in the degradation product of the cell component is preferably corrected in consideration of the influence of integration of a compound in the medium into the cell component, which compound is identical to the intracellular metabolite and unlabeled with an isotope. For example, when the cell component is a protein, the integration of an amino acid unlabeled with an isotope in the medium into the cellular protein is corrected when a metabolic flux is calculated by using analytical values of isotope distributions in cellular protein-hydrolyzed amino acids.

According to the condition (e-b), when a compound which is identical to an intracellular metabolite and unlabeled with an isotope is contained in the medium, the rate at which it is taken up into cells is analyzed. Then, the influence on the isotope distribution in an intracellular useful compound and/or a major metabolic intermediate thereof is corrected on the assumption that the rate obtained by subtracting the rate used for a cell component from the uptake rate is a flux for a flow into the decomposition pathway. As for the correction method, the analytical value of the isotope distribution in the intracellular metabolite may be corrected based on the flux for the flow into the decomposition pathway, or the aforementioned flow rate may be included in the intracellular metabolic flux model. In this embodiment, the compound that is not labeled with an isotope is preferably an amino acid (preferably isoleucine).

According to the condition (e-c), the carbon balance is calculated on the assumption that the total carbon dioxide partial pressure in a culture broth is completely derived from carbon dioxide discharged from cells as a result of consumption of the isotope-labeled substrate.

In a preferred embodiment of the present invention, correction or assumption is performed so that any one of the aforementioned conditions is satisfied. This can reduce analytical errors in the metabolic flux analysis using the isotope-labeled compound.

The cells to be analyzed with respect to the metabolic flux are preferably those of a microorganism having an ability to produce a useful compound. Examples of the cells include those of Escherichia coli, coryneform bacteria and Bacillus bacteria. The term "useful compound" used herein means compounds useful for seasoning, feed additives and pharmaceuticals, such as, amino acids, organic acids and nucleic acids.

The term "major metabolic intermediate" used herein means all metabolic intermediates included in metabolic flux analysis model, such as pyruvate, glucose-6-phosphate, fructose-6-phosphate, oxaloacetate, and so on.

In the present invention, cultivation method of the cells is preferably batch culture or fed-batch culture. The batch culture is a closed system culture method with specific nutrient types, whereas the fed-batch culture is a culture method in which a feeding medium containing a substrate is continuously or intermittently added to the culture system. The analysis method of the present invention can be applied if the culture is batch culture or fed-batch culture.

The intracellular metabolite of which isotope distribution is measured is preferably an amino acid and/or organic acid and/or major metabolic intermediate thereof.

The present invention also provides a program for executing the analysis method of the present invention. The program of the present invention causes a computer to function as (I) a means for storing data of isotope distribution measured by the following steps (a) to (c):
(a) the step of culturing cells in a medium not containing any isotope-labeled substrate to a target phase of a metabolic flux analysis,
(b) the step of adding an isotope-labeled substrate to the medium, and continuing culture and collecting samples from the medium in time course, and
(c) the step of measuring isotope distribution in a intracellular metabolite contained in the samples collected in time course,
(II) a means for performing a regression analysis for stored data to calculate an isotope distribution ratio of a steady state, and
(III) a means for analyzing a metabolic flux of the cultured cells by using the calculated isotope distribution ratio.

The data of isotope distribution measured by the steps (a) to (c) (labeled substrate pulse addition system) are usually inputted by using a data inputting means such as a keyboard or a means for transmitting data from a storage medium or via a transmission medium.

The means for performing a regression analysis for the stored data and calculate an isotope distribution ratio of a steady state may be a means suitable for performing the calculation step explained for the analysis method of the present invention.

The means for analyzing a metabolic flux of cultured cells by using the calculated isotope distribution ratio may be a means suitable for performing the analysis step explained for the analysis method of the present invention. The results of the analysis are usually outputted by a display means such as display devices or a means for transmitting data to a storage medium or via a transmission medium.

The program of a preferable embodiment is a program for causing a computer to function also as, in addition to the means of (I) to (III) mentioned above, a means for storing an intracellular metabolic flux model constructed for an intracellular metabolic flux to be analyzed, a means for inputting analytical values of cells cultured in a medium containing an isotope-labeled substrate as a carbon source, a means for determining a variable of the intracellular metabolic flux model based on the intracellular metabolic flux model and the analytical values of cells to determine the intracellular metabolic flux and a means for outputting the determined intracellular metabolic flux, wherein the intracellular metabolic flux model is constructed, and/or the variable of the intracellular metabolic flux model is calculated so that at least one of the aforementioned conditions (e-a) to (e-c) should be satisfied.

The intracellular metabolic flux model constructed for the intracellular metabolic flux to be analyzed and the analytical values of cells cultured in a medium containing an isotope-labeled substrate as a carbon source are as explained for the analysis method of the present invention. The intracellular metabolic flux model is usually stored in a format of data usually used for representation of intracellular metabolic flux models. For example, when the metabolic flux model is represented by a stoichiometric matrix, the model data are stored as a matrix. The means for inputting analytical values include a means for transmitting data from a storage medium or via a transmission medium.

The means for determining a variable of the intracellular metabolic flux model based on the intracellular metabolic flux model and analytical values of cells to determine the intracellular metabolic flux may be a means suitable for performing the determination step explained in the analysis method of the present invention.

The means for outputting the determined intracellular metabolic flux includes a means for transmitting data to a storage medium or via a transmission medium. The output of the intracellular metabolic flux may be a chart showing a metabolic network for which the metabolic flux model is constructed and displaying flux values at positions corresponding to respective reactions in the metabolic network in the chart.

Figure 7:
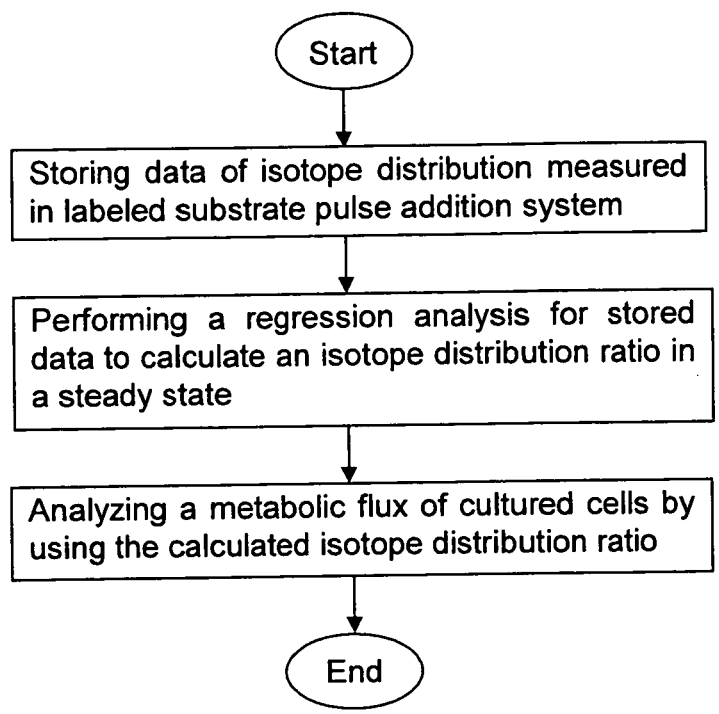
FIG. 7 shows a flowchart of a metabolic flux analysis program.

The flowchart of the program of the present invention is shown in FIG. 7. The steps (a) to (c) in (I) mentioned above and preferred embodiments thereof are as explained for the steps (a) to (c) in the analysis method of the present invention, the means of (II) mentioned above and preferred embodiments thereof are as explained for the step (d) in the analysis method of the present invention, and the means of (III) mentioned above and preferred embodiments thereof are as explained for the step (e) in the analysis method of the present invention, respectively. The program of the present invention can be prepared according to a usual programming method except that the intracellular metabolic flux model is constructed, and/or the variable of the intracellular metabolic flux model is calculated so that they should satisfy the aforementioned conditions.

In another aspect of the present invention, it is provided that a computer-readable recording medium in which the program according to the present invention is stored. The program according to the present invention can also be stored in a computer-readable recording medium. The term "recording medium" used herein includes arbitrary "removable physical media" such as flexible disc, magneto-optical disc, ROM, EPROM, EEPROM, CD-ROM, MO and DVD, arbitrary "fixed physical media" such as ROM, RAM and HD built in various computer systems and "communication media" for temporarily storing a program such as communication circuits and carrier waves for transmitting a program via a network represented by LAN, WAN and the Internet.

Further, the "program" is one for processing data written in an arbitrary language or operation notation, and its format such as source code or binary code is not limited. The "program" is not necessarily limited to a single program, and includes a program described in a distributed architecture comprising two or more modules or libraries or achieves its function by cooperating with a separate program represented by Operating System (OS). Well-known configurations and procedures can be used as specific configurations for reading the program stored in a recording medium, reading procedures, installation procedures after reading and so forth in each device shown in the embodiments.

EXAMPLE 1

The bacterial strains and media shown below were used.
(1) *Escherichia coli* Strain and Plasmid Bacterial strain: WYK050 (a strain derived from *Escherichia coli* wild strain W3110, which is resistant to S-(2-aminoethyl)cysteine and deficient in lysine decomposition genes, ldc and cadA genes (Kikuchi, Y. et al. J. Bacteriol., 179, pp. 4486-4492, 1997))

Plasmid: pCAB1 (obtained by incorporating lysC, dapA and dapB genes derived from *Escherichia coli* into vector RSF1010)

A bacterial strain obtained by introducing pCAB1 into WYK050 was used for cultivation.
(2) Media LB agar medium: 1.0% Bacto tryptone, 0.5% Bacto yeast extract, 1% NaCl, 1.5% agar. If necessary, 20 µg/ml of streptomycin was added.

Main culture medium: 16 g/L of ammonium sulfate, 3 g/L of potassium dihydrogenphosphate, 4 g/L of yeast extract, 10 mg/L of iron sulfate heptahydrate, 10 mg/L of manganese sulfate pentahydrate, 400 mg/L of isoleucine, 40 g/L of glucose, 1 g/L of magnesium sulfate heptahydrate. pH was adjusted to 7.0 with potassium hydroxide. If necessary, 20 µg/ml of streptomycin was added. The main culture medium was used for liquid culture of *Escherichia coli*. Feeding solution: 500 g/L of glucose, 80 g/L of ammonium sulfate.

(1) Construction of Metabolic Flux Analysis Model

A stoichiometric equation for calculating a metabolic flux was developed by assuming a quasi-steady state of intracellular metabolic intermediates (Savinell and Palsson, Journal of Theoretical Biology, 154, pp. 421-454, 1992; Vallino and Stephanopoulos, Biotechnology and Bioengineering, 41, pp. 633-646, 1993). Formulas of the reactions included in this model are as shown in Table 2. Explanations of the abbreviations are given in Table 1. Some reactions without branching were consolidated to simplify the formula. Since the pentose phosphate pathway is complicated, it was represented by using two formulas. For biomass composition, previously reported data was used (Neidhardt et al., Physiology of the Bacterial Cell, 1990). Further, the composition of amino acids in intracellular proteins was obtained from the concentration ratios of the amino acids obtained by actually hydrolyzing the intracellular proteins. The stoichiometric matrix of this model has a degree of freedom of 8, and 7 fluxes other than the sugar consumption rate must be determined to obtain a solution. The following 7 fluxes were defined as the free fluxes: bacterial cell production rate, lysine production rate, acetic acid production rate, formic acid production rate, ICL flux, G6PDH flux and malic enzyme flux. The results of the cell production rate and various production rates were obtained from the cultivation experiment. Further, the remaining 3 fluxes were determined by an optimization algorithm based on measured values of the isotope distributions in amino acids and so forth (described later). Further, the constructed model includes 14 reversible reactions. Their reversibilities were defined as exchange coefficients that can be represented by numerical values of 0 to 1 (Dauner et al., Biotechnology and Bioengineering, 76, pp. 144-156, 2001; Wiechert and de Graaf, Biotechnology and Bioengineering, 55, pp. 101-117, 1997). These exchange coefficients are also variables determined based on the measured values of the isotope distributions as the aforementioned 3 free fluxes. As for neighboring reactions in the glycolysis, pentose phosphate pathway and TCA cycle, the reversibilities were assumed to be equal for simplification. Since the results of sensitivity analysis revealed that the reactions 9, 29 and 30 in the reaction list of Table 2 had little influence on the isotope distributions, the values were assumed to be 0. From the above, reversible reactions of which exchange coefficients were to be determined were 6 reactions.

To calculate isotopomer distribution vectors (IDV) of all the substances in the model, an isotopomer balance equation was developed as a function of free fluxes and exchange coefficients and isotopomer distributions in substrates. A column vector called IDV represents proportions of isotopomers, and the sum of elements is 1 (Schmidt et al., Biotechnology and Bioengineering, 55, pp. 831-840, 1997; Wittmann and Heinzle, Biotechnology and Bioengineering, 62, pp. 739-750, 1999). The isotopomer balance equation is described by using an isotopomer mapping matrix (IMM) explained in more detail by Schmidt et al. (Schmidt et al., Biotechnology and Bioengineering, 55, pp. 831-840, 1997). An atom mapping matrix (AMM) is a matrix representing transfer of carbon atoms from a reactant to a product. Based on this, the isotopomer mapping matrix (IMM), which represents transfer of isotopomers from a reactant to a product, is computed by using MATLAB (The MathWorks, Natick, Mass.), which is a mathematical software.

The isotopomer balance equation can be solved by using the Gause-Seidel iteration method with the free fluxes and exchange coefficients as inputs.

In addition to consumption of glucose, a microbial cell takes up carbon dioxide and consumes acetic acid during the growth. Since carbon dioxide is also produced from metabolism of isotope-labeled glucose, some percentages of carbon dioxide consist of $^{13}C$-carbon dioxide. The percentage was calculated according to a carbon dioxide balance equation taking all the reactions producing carbon dioxide into consideration. Although accurate value varies depending on the intracellular metabolic flux distribution, it was generally about 32%. In this calculation, it was assumed that carbon dioxide from air was not consumed. This is because the concentration of carbon dioxide produced by the cells as a result of consumption of isotope-labeled glucose is very high (in the experiment, the concentration of exhausted carbon dioxide reached 4 to 5%), and therefore it may be considered that the total carbon dioxide partial pressure in a fermenter should be attributable to carbon dioxide exhausted from the cells.

Although isotopomer distributions cannot be obtained for all of the substances from the mass spectrometry analysis, mass distributions can be obtained. This information is represented as mass distribution vector (MDV), and each element includes an isotopomer having an identical mass (Wittman and Heinzle, Biotechnology and Bioengineering, 62, pp. 739-750, 1999). Therefore, for a substance having n of carbon atoms, MDV contains n+1 of elements. MDV can be calculated by adding up elements having an identical mass among those in IDV. To what degree the result of the model matches the experimental value can be evaluated by comparing the MDV calculated as described above with the MDV obtained from the experiment.

TABLE 1

| | |
|---|---|
| μ | Specific growth rate [$h^{-1}$] |
| ν | Specific sugar consumption rate [g/g/h] |
| ρ | Specific lysine production rate [g/g/h] |
| YE | Yeast extract |
| ldc | *E. coli* lysine decarboxylase gene (Constitutive) |
| cadA | *E. coli* lysine decarboxylase gene (Inducible) |
| lysC | *E. coli* aspartate kinase III gene |
| dapA | *E. coli* dihydrodipicolinate synthase gene |
| dapB | *E. coli* dihydrodipicolinate reductase gene |
| CT | Cultivation time |
| ICL | Isocitrate lyase |
| PP pathway | Pentose phosphate pathway |
| PEPC | Phosphoenolpyruvate carboxylase |
| ICD | Isocitrate dehydrogenase |
| DDH | meso-Diaminopimelate dehydrogenase |
| G6PDH | Glucose-6-phosphate dehydrogenase |
| 3PG | 3-Phospho-D-glyceric acid |
| AcCoA | Acetyl coenzyme A |
| AcOH | Acetic acid |
| aIVA | α-Keto-isovaleric acid |
| aKG | 2-Oxoglutaric acid |
| Ala | Alanine |
| Arg | Arginine |
| Asn | Asparagine |
| Asp | Aspartic acid |
| CHR | Chorismic acid |
| Cit | Citric acid |
| CO2 | Carbon dioxide |
| Cys | Cysteine |
| E4P | Erythrose-4-phosphate |
| extraC1 | Carbon atom derived from ATP curing histidine synthesis |
| F6P | Fructose-6-phosphate |
| Form | Formic acid |
| Fum | Fumaric acid |
| G6P | Glucose-6-phosphate |
| GAP | Glyceraldehyde-3-phosphate |
| Glc | Glucose |
| Gln | Glutamine |
| Glu | Glutamic acid |
| Gly | Glycine |
| His | Histidine |
| Ile | Isoleucine |
| Leu | Leucine |
| Lys | Lysine |
| Lysext | Lysine product (secreted) |
| Mal | Malic acid |
| Met | Methionine |
| mTHF | Methyltetrahydrofolic acid |
| NH3 | Ammonia |
| OAA | Oxaloacetatic acid |
| PEP | Phosphoenolpyruvic acid |
| Phe | Phenylalanine |
| Pro | Proline |
| PRPP | Phosphoribosyl pyrophosphate |
| Pyr | Pyruvic acid |
| R5P | Pentose phosphate pool |
| SDAP | N-Succinyl-L-2,6-diaminoheptanedioate |
| Ser | Serine |
| Suc | Succinic acid |
| THF | Tetrahydrofolic acid |
| Thr | Threonine |
| Trp | Tryptophan |
| Tyr | Tyrosine |
| Val | Valine |

TABLE 2

Reaction formulas used for metabolic model

| [1] | | Glc + PEP -> G6P + Pyr |
|---|---|---|
| [2] | | G6P -> R5P + CO2 |
| [3] | (r) | 3R5P -> 2F6P + GAP |
| [4] | (r) | 2R5P -> F6P + E4P |
| [5] | (r) | G6P -> F6P |
| [6] | (r) | F6P -> 2GAP |
| [7] | (r) | GAP -> 3PG |
| [8] | (r) | 3PG -> PEP |
| [9] | (r) | PEP -> Pyr |
| [10] | | Pyr + CoA -> AcCoA + CO2 |
| [11] | (r) | PEP + CO2 -> OAA |
| [12] | | AcCoA -> AcOH + CoA |
| [13] | | AcCoA + OAA -> Cit + CoA |
| [14] | (r) | Cit -> aKG + CO2 |
| [15] | | aKG + $NH_3$ -> Glu |
| [16] | | aKG -> Suc + CO2 |
| [17] | | Cit + AcCoA -> Mal + Suc + CO2 + CoA |
| [18] | (r) | Succ -> Mal |
| [19] | (r) | Mal -> OAA |
| [20] | | OAA + Glu -> Asp + aKG |
| [21] | | Asp + Pyr -> Lys + CO2 |
| [22] | | Asp + Pyr + Glu -> Lys + aKG + CO2 |
| [23] | | Glu + NH3 -> Gln |
| [24] | | Glu -> Pro |
| [25] | | Glu + Gln + Asp + AcCoA + CO2 -> Arg + aKG + FUM + CoA |
| [26] | | Asp + Cys + mTHF -> Met + CoA + THF + Pyr + NH3 |
| [27] | | Asp -> Thr |
| [28] | | Thr + Glu + Pyr -> Ile + aKG + NH3 + CO2 |
| [29] | (r) | 3PG > Ser |
| [30] | (r) | Ser + THF -> Gly + mTHF |
| [31] | | 2PEP + E4P -> CHR |
| [32] | | CHR + Glu -> Tyr + CO2 + aKG |
| [33] | | CHR + Glu -> Phe + CO2 + aKG |
| [34] | | CHR + R5P + Ser + Gln -> Trp + Glu + Pyr + CO2 + GAP |
| [35] | | 2Pyr -> aIVA + CO2 |
| [36] | | aIVA + Glu -> Val + aKG |
| [37] | | Val + Pyr -> Ala + aIVA |
| [38] | | aIVA + AcCoA + Glu -> Leu + CO2 + aKG + CoA |
| [39] | | PRPP + Gln + extraC1 -> His + aKG |
| [40] | | Ser + AcCoA + H2S -> Cys + AcOH |
| [41] | | Asp + NH3 -> Asn |
| [42] | (r) | Mal -> Pyr + CO2 |
| [43] | | R5P -> PRPP |
| [44] | | mTHF -> Form |
| [45] | | Gly -> CO2 + mTHF |
| [46] | | Ile + CO2 -> Thr + Pyr |

(r): Reversible reaction (2) Correction of Influences by Naturally Occurring Isotopes of Carbon, Hydrogen, Nitrogen and Oxygen Atoms A program was prepared according to the paper of Heizle et al. (Wittman and Heinzle, Biotechnology and Bioengineering, 62, pp. 739-750, 1999) and used to correct influences by naturally occurring isotopes of hydrogen, carbon, nitrogen and oxygen for the total analytical data.

The calculation was performed by using ratios of naturally occurring isotopes of carbon, hydrogen, nitrogen and oxygen, i.e., $^1H=0.99985$, $^2H=0.015$, $^{12}C=0.98893$, $^{13}C=0.01107$, $^{14}N=0.99634$, $^{15}N=0.00366$, $^{16}O=0.99759$, $^{17}O=0.00037$ and $^{18}O=0.00204$. Matrices for correction of naturally occurring isotopes of hydrogen, carbon and nitrogen can be described as follows, wherein α is an existing ratio of a low mass isotope, β is an existing ratio of a high mass isotope (these satisfy the condition of α+β=1), ρni is a corresponding binomial coefficient, and E1 is a substance name.

$$CMDV, E1 = \begin{pmatrix} \rho_{n1}*\alpha^n & 0 & 0 & \cdots \\ \rho_{n2}*\alpha^{n-1}*\beta^1 & \rho_{n1}*\alpha^n & 0 & \cdots \\ \rho_{n3}*\alpha^{n-2}*\beta^2 & \rho_{n2}*\alpha^{n-1}*\beta^1 & \rho_{n1}*\alpha^n & \cdots \\ \cdots & \cdots & \cdots & \cdots \end{pmatrix}$$

$$CMDV,^{18}O = \begin{pmatrix} \rho_{n1}*\alpha^n & 0 & 0 & \cdots \\ 0 & \rho_{n1}*\alpha^n & 0 & \cdots \\ \rho_{n3}*\alpha^{n-2}*\beta^2 & 0 & \rho_{n1}*\alpha^n & \cdots \\ \cdots & \cdots & \cdots & \cdots \end{pmatrix}$$

(3) Optimization of Metabolic Flux

A program was constructed in which MDV was calculated by using the isotopomer balance equation with free fluxes and exchange reaction fluxes as input values, and the previously inputted values of free fluxes and exchange reaction fluxes were optimized by the evolutionary algorithm (Stephani et al., Journal of Theoretical Biology, 199, pp. 45-61, 1999) so that the sum of squares of the difference from the MDV obtained by the experiment should be minimized. In this program, the variables to be optimized in the isotope-labeled substrate initial addition system used as a reference for comparison were fluxes of ICL, malic enzyme, pentose phosphate pathway (G6PDH), values of 6 exchange reactions and Pex, which represents an exchange reaction of a protein and intracellular amino acid pools.

In the isotope-labeled substrate pulse addition system, Pex was set as a variable peculiar to all of the amino acids and incorporated into the isotopomer balance equation described in (1) mentioned above in the aforementioned program. The bacterial cell yield and lysine yield were set so that 20% deviation from the input values should be accepted in order to take measurement errors in the experiment into account. To reduce the computation time, some modifications were made in a general evolutionary algorithm. Since 50,000 elements and 200 generations were found to be optimal to search the minimum value in the space of solution as a result of various examinations, these set values were used for the analyses.

(4) Sensitivity Analysis

The confidence interval of free flux depends not only on variance of measured values, but also on the Jacobian matrix. The Jacobian matrix shows degree of how easily each IDV changes when the free flux changes near the optimal value. A Jacobian matrix was prepared based on the constructed metabolic analysis model, and sensitivity analysis was performed according to the method of Mollney et al. (Biotechnology and Bioengineering, 66, pp. 86-103) in order to find an optimum mixing ratio of labeled glucose. The labeled glucose used was limited to 1-$^{13}$C-Glc and U-$^{13}$C-Glc to perform the calculation. As a result, a result was obtained that a mixing ratio of 50:50 in terms of molar percentage should be optimal.

(5) Cultivation Experiment

A suspension of cells of the WYK050/pCAB1 strain was streaked on the LB agar medium, and the cells were cultured as stationary culture at 37° C. for 24 hours. Cells from two of the stationary culture plates were inoculated into the seed culture medium. The seed culture was terminated when the initially added sugar was completely consumed, and the culture broth was inoculated to the main culture medium to perform the main culture. The same medium composition was used for the seed culture and the main culture, and it was the composition described above as the main culture medium. For the cultivation, a 1-L jar fermenter was used, and non-labeled glucose was used as the substrate for the isotope-labeled substrate pulse addition system. For the isotope-labeled substrate initial addition system, labeled glucose was used (1-$^{13}$C-Glc:U-$^{13}$C-Glc=5:5). The initial liquid volume of the cultivation was 300 ml, and the temperature and pH were regulated to be 37° C. and 6.7, respectively. Ammonia gas was used to regulate pH. Aeration was controlled at 300 ml/min. The stirring rate was suitably regulated so that the dissolved oxygen concentration of the culture broth should be always maintained at 5% or higher. Feeding of a sugar solution (feeding solution) was started at 17 hours after the start of the cultivation. The feeding rate was suitably regulated so that the sugar concentration in the medium should be 5 g/L or lower. Fermentation samples were obtained at 17 hours and 25 hours after the start of the cultivation. For the isotope-labeled substrate initial addition system as the control for comparison, amino acids produced by hydrolysis of cellular proteins were also measured for each sample for correction. For the isotope-labeled substrate pulse addition system, the feeding of non-labeled glucose was terminated immediately before the collection of samples, and depletion of the sugar was waited. At the instant of the start of increase of the dissolved oxygen concentration due to depletion of the sugar, 2 g of labeled glucose (1-$^{13}$C-Glc:U-$^{13}$C-Glc=5:5) prepared beforehand was added, and samples were collected 1, 5, 10 and 30 minutes after the addition, which was considered 0 minute. Immediately after the collection of the samples, intracellular metabolites were extracted from the cells of the samples. Isotope distribution was measured for each amino acid by using LC-MS.

(6) Prediction of Isotope Ratios in Amino Acids in Isotope Steady State in Pulse Addition Experiment System Based on MS analytical data for isotope distribution ratios in the amino acids at various time points after the pulse addition of the isotope-labeled substrate, regression analysis was performed by using a function of $MDV(M_i)_\xi = \{(a*t^\lambda + b)/(d + c*t^\lambda)\}^\eta$. $\xi$ is a substance name, a, b, c and d are corresponding regression parameters, and $\xi$ and $\eta$ are external parameters. $MDV(M_i)$ represents an existing ratio of a mass M+i of the substance $\xi$. When the carbon number of the substance $\xi$ is n, i is an integer of 0 to n and satisfies the condition of $\Sigma MDV(M_i)=1$. The external parameters $\xi$ and $\eta$ were selected from the search ranges of 0.1 to 2 with an interval of 0.1 and 1 to 20 with an interval of 1, respectively, and 400 combinations thereof in total were used for the analysis to calculate regression parameters providing a minimum nonlinear regression error for each amino acid. The results are shown in Table 3. As typical examples, the results of regression analysis after 17 hours and 25 hours of cultivation obtained by using the obtained regression parameters are shown in FIG. 1 for alanine and glycine. By using the regression parameters a, b, c and d obtained by the nonlinear regression analysis together with the time t considered infinite, $MDV(M_i)_\xi$ was calculated to predict MDV of each amino acid of which isotope distribution is in a steady state. The amino acid MDV experimental values for isotope distributions in a steady state obtained as a result are shown in Table 6.

(7) Metabolic Flux Analysis

By using MDV of each amino acid obtained by the method of (6) mentioned above, metabolic fluxes were calculated according to the method of (3) mentioned above. The values of extracellular lysine production rate and acetic acid production rate as well as cell production rate-standardized with the sugar consumption rate, which were used for the optimization of metabolic fluxes, are shown in Table 4.

The free fluxes obtained as a result of the analyses at 17 hours and 25 hours after the start of cultivation in the isotope-labeled glucose initial addition system and the isotopic-labeled glucose pulse addition system are shown in Table 5, and all metabolic flux distributions calculated based on the free fluxes are shown in FIGS. 2 to 5. The calculated MDV values for each amino acid obtained by the metabolic flux analysis are shown in Table 6. The calculated MDV values well coincided with the experimental MDV values obtained in (6) mentioned above.

TABLE 3

|  | λ | η | error |  | M | M+1 | M+2 | M+3 | M+4 | M+5 | M+6 | M+7 | M+8 | M+9 | M+10 |
|---|---|---|---|---|---|---|---|---|---|---|---|---|---|---|---|
| At 17 hours from the start of cultivation ||||||||||||||||
| Gly | 0.7 | 1 | 0.025 | a | 1.312 | 0.048 | 0.009 | | | | | | | | |
|  |  |  |  | b | 0.598 | 0.172 | 0.602 | | | | | | | | |
|  |  |  |  | c | 1.106 | 1.527 | 1.736 | | | | | | | | |
|  |  |  |  | d | 1.354 | 1.800 | 2.145 | | | | | | | | |
| Ala | 0.7 | 1 | 0.019 | a | 0.538 | 0.038 | 0.007 | 0.000 | | | | | | | |
|  |  |  |  | b | 0.632 | 0.863 | 0.116 | 0.854 | | | | | | | |
|  |  |  |  | c | 1.955 | 3.576 | 1.614 | 2.330 | | | | | | | |
|  |  |  |  | d | 0.562 | 1.003 | 1.634 | 0.509 | | | | | | | |
| Val | 0.4 | 12 | 0.051 | a | 1.040 | −0.473 | 0.089 | 0.063 | −0.032 | −0.022 | | | | | |
|  |  |  |  | b | 1.159 | 1.977 | 1.733 | −5.156 | 1.751 | 1.584 | | | | | |
|  |  |  |  | c | 1.416 | 2.303 | 1.981 | −5.788 | 2.067 | 1.820 | | | | | |
|  |  |  |  | d | 1.045 | −0.600 | 0.138 | −0.124 | 0.078 | 0.044 | | | | | |
| Asp | 1 | 1 | 0.147 | a | 1.600 | 0.112 | 0.027 | 0.009 | 0.007 | | | | | | |
|  |  |  |  | b | 0.028 | 0.292 | 0.116 | 0.292 | 0.047 | | | | | | |
|  |  |  |  | c | 0.298 | 1.512 | 0.399 | 1.436 | 0.151 | | | | | | |
|  |  |  |  | d | 1.754 | 2.389 | 3.814 | 1.810 | 4.168 | | | | | | |
| Gln | 1.4 | 4 | 0.092 | a | 3.723 | 2.013 | −2.892 | −4.333 | 1.409 | 0.937 | | | | | |
|  |  |  |  | b | 0.031 | 1.253 | −2.065 | −0.898 | 0.157 | 0.083 | | | | | |
|  |  |  |  | c | 0.053 | 1.592 | −2.463 | −1.035 | 0.185 | 0.102 | | | | | |
|  |  |  |  | d | 3.757 | 2.887 | −5.400 | −8.113 | 2.827 | 2.056 | | | | | |
| Phe | 0.9 | 2 | 0.041 | a | 9.208 | 0.734 | 0.183 | 0.110 | 0.074 | −0.043 | 0.106 | −0.040 | −0.034 | 0.041 | |
|  |  |  |  | b | 1.522 | 0.123 | 0.365 | 0.438 | 0.503 | 0.646 | 0.477 | 0.517 | 0.369 | 0.259 | |
|  |  |  |  | c | 2.649 | 0.489 | 1.520 | 1.517 | 1.714 | 2.035 | 1.507 | 1.942 | 1.697 | 1.269 | |
|  |  |  |  | d | 9.718 | 2.372 | 1.978 | 2.142 | 2.135 | 1.826 | 2.568 | 1.851 | 1.956 | 2.086 | |
| Tyr | 1.2 | 1 | 0.054 | a | 1.567 | 0.170 | 0.022 | 0.003 | 0.001 | 0.001 | 0.000 | 0.001 | 0.000 | 0.002 | |
|  |  |  |  | b | 0.197 | 0.091 | 0.031 | 0.058 | 0.061 | 0.066 | 0.051 | 0.038 | 0.018 | 0.014 | |
|  |  |  |  | c | 0.435 | 1.331 | 0.716 | 0.965 | 0.874 | 0.762 | 0.618 | 0.604 | 0.458 | 0.374 | |
|  |  |  |  | d | 1.758 | 1.773 | 2.351 | 2.305 | 2.441 | 2.721 | 2.830 | 2.689 | 2.501 | 2.453 | |

TABLE 3-continued

| | λ | η | error | | M | M + 1 | M + 2 | M + 3 | M + 4 | M + 5 | M + 6 | M + 7 | M + 8 | M + 9 | M + 10 |
|---|---|---|---|---|---|---|---|---|---|---|---|---|---|---|---|
| Trp | 0.8 | 9 | 0.058 | a | 1.699 | 1.382 | −0.286 | 0.010 | 0.078 | −0.044 | −0.043 | 0.065 | −0.023 | −0.105 | −0.100 |
| | | | | b | 0.761 | 0.237 | 1.416 | 1.884 | 1.610 | 2.109 | 1.949 | 2.505 | 1.633 | 1.987 | 1.709 |
| | | | | c | 0.954 | 0.361 | 2.037 | 2.533 | 2.096 | 2.655 | 2.437 | 3.143 | 2.097 | 2.615 | 2.434 |
| | | | | d | 1.725 | 1.751 | −0.474 | 0.023 | 0.193 | 0.124 | 0.143 | 0.436 | 0.251 | 0.272 | 0.257 |
| Met | 1.1 | 1 | 0.214 | a | 1.198 | 0.127 | 0.011 | −0.003 | −0.002 | 0.019 | | | | | |
| | | | | b | 0.277 | −1.667 | 0.191 | 0.133 | 0.084 | 0.030 | | | | | |
| | | | | c | 1.156 | −7.622 | 1.115 | 0.671 | 0.398 | 0.234 | | | | | |
| | | | | d | 1.282 | 2.211 | 2.361 | 3.981 | 4.149 | 2.984 | | | | | |
| At 25 hours from the start of cultivation | | | | | | | | | | | | | | | |
| Gly | 1 | 2 | 0.038 | a | 2.849 | −0.035 | −0.020 | | | | | | | | |
| | | | | b | 5.621 | 0.904 | 1.232 | | | | | | | | |
| | | | | c | 7.421 | 2.211 | 2.426 | | | | | | | | |
| | | | | d | 2.894 | 0.212 | 0.308 | | | | | | | | |
| Ala | 1.3 | 1 | 0.032 | a | 0.591 | 0.040 | 0.007 | 0.000 | | | | | | | |
| | | | | b | 0.673 | 0.780 | 0.151 | 0.727 | | | | | | | |
| | | | | c | 1.893 | 3.383 | 1.741 | 2.213 | | | | | | | |
| | | | | d | 0.616 | 1.058 | 1.454 | 0.566 | | | | | | | |
| Val | 1.3 | 6 | 0.148 | a | 0.573 | −1.950 | −0.003 | 0.093 | 0.045 | 0.032 | | | | | |
| | | | | b | 1.581 | 0.318 | 1.506 | 2.355 | 1.463 | 1.625 | | | | | |
| | | | | c | 1.920 | 0.448 | 2.039 | 3.147 | 2.238 | 2.377 | | | | | |
| | | | | d | 0.580 | −2.825 | −0.007 | 0.311 | 0.163 | 0.127 | | | | | |
| Asp | 1 | 8 | 0.085 | a | 3.570 | −2.324 | 1.844 | 1.615 | 1.012 | | | | | | |
| | | | | b | 0.094 | −1.201 | 0.766 | 0.370 | 0.375 | | | | | | |
| | | | | c | 0.122 | −1.484 | 0.898 | 0.439 | 0.468 | | | | | | |
| | | | | d | 3.606 | −3.383 | 3.399 | 2.586 | 2.455 | | | | | | |
| Gln | 1.6 | 2 | 0.083 | a | 3.964 | 1.105 | −0.557 | 0.231 | 0.113 | 0.074 | | | | | |
| | | | | b | 0.016 | 0.709 | −0.612 | 0.067 | 0.041 | 0.020 | | | | | |
| | | | | c | 0.084 | 1.768 | −1.213 | 0.119 | 0.084 | 0.052 | | | | | |
| | | | | d | 4.123 | 4.620 | −5.982 | 3.540 | 3.459 | 3.273 | | | | | |
| Phe | 1 | 1 | 0.052 | a | 1.702 | 0.219 | 0.024 | 0.006 | 0.007 | 0.005 | 0.006 | 0.003 | 0.003 | 0.003 | |
| | | | | b | 0.054 | 0.004 | 0.006 | 0.011 | 0.009 | 0.012 | 0.010 | 0.007 | 0.004 | 0.002 | |
| | | | | c | 0.108 | 0.058 | 0.119 | 0.216 | 0.134 | 0.172 | 0.140 | 0.109 | 0.089 | 0.054 | |
| | | | | d | 1.933 | 2.269 | 2.366 | 2.516 | 2.600 | 2.694 | 2.652 | 2.567 | 2.380 | 2.314 | |
| Tyr | 0.3 | 1 | 0.012 | a | 6.216 | 0.507 | 0.214 | −0.033 | 0.057 | 0.051 | 0.007 | 0.025 | −0.021 | −0.025 | |
| | | | | b | −0.801 | 0.382 | −0.014 | 0.316 | 0.179 | 0.212 | 0.260 | 0.173 | 0.187 | 0.189 | |
| | | | | c | −0.713 | 1.355 | −0.338 | 1.330 | 0.437 | 0.536 | 0.958 | 0.510 | 1.010 | 1.381 | |
| | | | | d | 6.575 | 1.638 | 2.193 | 1.808 | 2.260 | 2.299 | 2.062 | 2.198 | 1.933 | 1.661 | |
| Trp | 1 | 1 | 0.119 | a | 1.189 | 0.284 | 0.005 | 0.001 | 0.001 | 0.004 | 0.005 | 0.007 | 0.004 | 0.003 | 0.001 |
| | | | | b | 0.280 | 0.013 | 0.118 | 0.159 | 0.135 | 0.137 | 0.121 | 0.085 | 0.061 | 0.033 | 0.015 |
| | | | | c | 1.081 | 0.233 | 2.245 | 1.947 | 1.630 | 1.340 | 1.138 | 0.863 | 0.785 | 0.584 | 0.562 |
| | | | | d | 1.373 | 2.425 | 0.511 | 1.132 | 1.633 | 2.112 | 2.261 | 2.475 | 2.547 | 2.501 | 2.272 |
| Thr | 1.1 | 10 | 0.096 | a | 1.976 | 1.358 | 3.358 | 1.790 | 1.037 | | | | | | |
| | | | | b | 0.129 | 1.248 | 3.909 | 0.623 | 0.333 | | | | | | |
| | | | | c | 0.154 | 1.457 | 4.462 | 0.723 | 0.397 | | | | | | |
| | | | | d | 1.988 | 1.854 | 5.737 | 2.696 | 1.950 | | | | | | |

TABLE 4

| Labeled substrate initial addition system | | | | Labeled substrate pulse addition system | | | |
|---|---|---|---|---|---|---|---|
| CT | Biomass | Lys | AcOH | CT | Biomass | Lys | AcOH |
| 17 | 0.29 | 0.24 | 0.04 | 17 | 0.28 | 0.18 | −0.04 |
| 25 | 0.26 | 0.28 | −0.24 | 25 | 0.17 | 0.21 | −0.10 |

\* Unit of Biomass, AcOH and Lys is mmol/10 mmol-Glc
\* CT represents cultivation time, of which unit is "hour".

TABLE 5

| | Labeled substance initial addition system | |
|---|---|---|
| | Initial addition system At 17 hours from the start of cultivation | Initial addition system At 25 hours from the start of cultivation |
| Free flux | | |
| G6PDH | 3.694 | 0.701 |
| ICL | 3.966 | 5.853 |
| Malic enzyme Exchange coefficient | 0.085 | 2.000 |
| Pentose phosphate cycle | 0.105 | 0.232 |
| Glycolysis | 0.753 | 0.631 |
| PEPC | 0.000 | 0.000 |
| ICD | 0.000 | 0.000 |
| TCA cycle | 0.618 | 0.517 |
| Malic Enzyme | 0.210 | 0.184 |
| Pex (Protein degradation coefficient) | 0.012 | 0.008 |

| | Labeled substance pulse addition system | |
|---|---|---|
| | Pulse addition system At 17 hours from the start of cultivation | Pulse addition system At 25 hours from the start of cultivation |
| Free flux | | |
| G6PDH | 2.442 | 0.167 |
| ICL | 2.713 | 4.151 |

TABLE 5-continued

| | | |
|---|---|---|
| Malic enzyme Exchange coefficient | 1.139 | 1.592 |
| Pentose phosphate cycle | 0.163 | 0.418 |
| Glycolysis | 0.768 | 0.900 |
| PEPC | 0.125 | 0.200 |
| ICD | 0.040 | 0.155 |
| TCA cycle | 0.147 | 0.043 |
| Malic enzyme | 0.075 | 0.131 |
| Pex (Gly) | 0.2481 | 0.2799 |
| Pex (Ala) | 0.072 | 0.1967 |
| Pex (Val) | 0.0075 | 0.3 |
| Pex (Asp) | 0 | 0.054 |
| Pex (Gln) | 0 | 0 |
| Pex (Phe) | 0.3431 | 0.4499 |
| Pex (Tyr) | 0.4401 | 0.5985 |
| Pex (Trp) | 0.0978 | 0.2888 |
| Pex (17-hour Met/25-hour Thr) | 0.0497 | 0.0366 |

TABLE 6

| | | M | M+1 | M+2 | M+3 | M+4 | M+5 | M+6 | M+7 | M+8 | M+9 | M+10 |
|---|---|---|---|---|---|---|---|---|---|---|---|---|
| \multicolumn{13}{c}{Labeled substance initial addition system} | | | | | | | | | | | | |
| \multicolumn{13}{c}{At 17 hours from the start of cultivation} | | | | | | | | | | | | |
| Gly | Calculated | 0.422 | 0.131 | 0.447 | | | | | | | | |
| | Found | 0.441 | 0.151 | 0.409 | | | | | | | | |
| Ala | Calculated | 0.244 | 0.235 | 0.099 | 0.422 | | | | | | | |
| | Found | 0.264 | 0.244 | 0.087 | 0.405 | | | | | | | |
| Val | Calculated | 0.080 | 0.124 | 0.197 | 0.251 | 0.151 | 0.197 | | | | | |
| | Found | 0.078 | 0.111 | 0.181 | 0.249 | 0.177 | 0.203 | | | | | |
| Asp | Calculated | 0.072 | 0.171 | 0.272 | 0.263 | 0.221 | | | | | | |
| | Found | 0.119 | 0.147 | 0.262 | 0.268 | 0.205 | | | | | | |
| Gln | Calculated | 0.030 | 0.098 | 0.205 | 0.289 | 0.232 | 0.146 | | | | | |
| | Found | 0.037 | 0.097 | 0.200 | 0.280 | 0.227 | 0.158 | | | | | |
| Phe | Calculated | 0.049 | 0.044 | 0.073 | 0.116 | 0.137 | 0.166 | 0.152 | 0.123 | 0.077 | 0.062 | |
| | Found | 0.040 | 0.045 | 0.075 | 0.120 | 0.134 | 0.166 | 0.158 | 0.119 | 0.073 | 0.070 | |
| Tyr | Calculated | 0.048 | 0.045 | 0.074 | 0.117 | 0.137 | 0.166 | 0.153 | 0.122 | 0.078 | 0.062 | |
| | Found | 0.041 | 0.045 | 0.075 | 0.119 | 0.140 | 0.169 | 0.149 | 0.120 | 0.077 | 0.066 | |
| Trp | Calculated | 0.007 | 0.028 | 0.057 | 0.096 | 0.131 | 0.156 | 0.167 | 0.143 | 0.105 | 0.072 | 0.037 |
| | Found | 0.044 | 0.021 | 0.040 | 0.070 | 0.111 | 0.140 | 0.152 | 0.141 | 0.111 | 0.099 | 0.071 |
| Met | Calculated | 0.060 | 0.110 | 0.205 | 0.242 | 0.241 | 0.142 | | | | | |
| | Found | 0.047 | 0.117 | 0.201 | 0.233 | 0.256 | 0.145 | | | | | |
| \multicolumn{13}{c}{At 25 hours from the start of cultivation} | | | | | | | | | | | | |
| Gly | Calculated | 0.3669 | 0.1892 | 0.4439 | | | | | | | | |
| | Found | 0.3894 | 0.2125 | 0.3981 | | | | | | | | |
| Ala | Calculated | 0.228 | 0.229 | 0.128 | 0.415 | | | | | | | |
| | Found | 0.255 | 0.251 | 0.104 | 0.390 | | | | | | | |
| Val | Calculated | 0.069 | 0.121 | 0.197 | 0.248 | 0.172 | 0.193 | | | | | |
| | Found | 0.080 | 0.116 | 0.190 | 0.259 | 0.165 | 0.190 | | | | | |
| Asp | Calculated | 0.068 | 0.170 | 0.272 | 0.275 | 0.215 | | | | | | |
| | Found | 0.093 | 0.155 | 0.260 | 0.288 | 0.204 | | | | | | |
| Gln | Calculated | 0.027 | 0.095 | 0.206 | 0.292 | 0.239 | 0.139 | | | | | |
| | Found | 0.026 | 0.083 | 0.196 | 0.291 | 0.243 | 0.161 | | | | | |
| Phe | Calculated | 0.035 | 0.038 | 0.070 | 0.112 | 0.140 | 0.171 | 0.160 | 0.130 | 0.086 | 0.058 | |
| | Found | 0.020 | 0.038 | 0.077 | 0.122 | 0.136 | 0.170 | 0.160 | 0.125 | 0.085 | 0.069 | |
| Tyr | Calculated | 0.034 | 0.039 | 0.072 | 0.114 | 0.140 | 0.170 | 0.160 | 0.126 | 0.086 | 0.060 | |
| | Found | 0.025 | 0.043 | 0.075 | 0.122 | 0.136 | 0.172 | 0.155 | 0.122 | 0.081 | 0.068 | |
| Trp | Calculated | 0.004 | 0.021 | 0.048 | 0.086 | 0.126 | 0.157 | 0.173 | 0.152 | 0.116 | 0.077 | 0.039 |
| | Found | 0.020 | 0.012 | 0.032 | 0.062 | 0.112 | 0.141 | 0.153 | 0.153 | 0.132 | 0.101 | 0.082 |
| Thr | Calculated | 0.070 | 0.168 | 0.272 | 0.276 | 0.214 | | | | | | |
| | Found | 0.074 | 0.172 | 0.264 | 0.266 | 0.225 | | | | | | |
| \multicolumn{13}{c}{Labeled substance pulse addition system} | | | | | | | | | | | | |
| \multicolumn{13}{c}{At 17 hours from the start of cultivation} | | | | | | | | | | | | |
| Gly | Calculated | 0.575 | 0.086 | 0.339 | | | | | | | | |
| | Found | 0.540 | 0.113 | 0.347 | | | | | | | | |
| Ala | Calculated | 0.317 | 0.202 | 0.078 | 0.403 | | | | | | | |
| | Found | 0.322 | 0.241 | 0.072 | 0.365 | | | | | | | |
| Val | Calculated | 0.086 | 0.124 | 0.198 | 0.251 | 0.137 | 0.204 | | | | | |
| | Found | 0.087 | 0.156 | 0.196 | 0.244 | 0.133 | 0.184 | | | | | |
| Asp | Calculated | 0.105 | 0.218 | 0.205 | 0.234 | 0.238 | | | | | | |
| | Found | 0.086 | 0.177 | 0.266 | 0.186 | 0.286 | | | | | | |
| Gln | Calculated | 0.039 | 0.110 | 0.220 | 0.284 | 0.216 | 0.131 | | | | | |
| | Found | 0.002 | 0.082 | 0.175 | 0.262 | 0.253 | 0.226 | | | | | |
| Phe | Calculated | 0.360 | 0.032 | 0.055 | 0.081 | 0.088 | 0.112 | 0.092 | 0.081 | 0.050 | 0.049 | |
| | Found | 0.336 | 0.064 | 0.059 | 0.085 | 0.088 | 0.103 | 0.102 | 0.072 | 0.048 | 0.042 | |
| Tyr | Calculated | 0.454 | 0.028 | 0.047 | 0.069 | 0.075 | 0.095 | 0.079 | 0.069 | 0.042 | 0.042 | |
| | Found | 0.434 | 0.068 | 0.042 | 0.063 | 0.072 | 0.090 | 0.086 | 0.065 | 0.042 | 0.039 | |
| Trp | Calculated | 0.107 | 0.031 | 0.057 | 0.090 | 0.115 | 0.134 | 0.143 | 0.121 | 0.094 | 0.068 | 0.040 |
| | Found | 0.131 | 0.022 | 0.038 | 0.070 | 0.094 | 0.126 | 0.134 | 0.130 | 0.106 | 0.084 | 0.042 |
| Met | Calculated | 0.085 | 0.137 | 0.203 | 0.205 | 0.224 | 0.147 | | | | | |
| | Found | 0.023 | 0.191 | 0.183 | 0.148 | 0.175 | 0.189 | | | | | |

TABLE 6-continued

| | | M | M + 1 | M + 2 | M + 3 | M + 4 | M + 5 | M + 6 | M + 7 | M + 8 | M + 9 | M + 10 |
|---|---|---|---|---|---|---|---|---|---|---|---|---|
| | | | | | At 25 hours from the start of cultivation | | | | | | | |
| Gly | Calculated | 0.552 | 0.152 | 0.296 | | | | | | | | |
| | Found | 0.574 | 0.167 | 0.258 | | | | | | | | |
| Ala | Calculated | 0.383 | 0.182 | 0.138 | 0.298 | | | | | | | |
| | Found | 0.346 | 0.233 | 0.090 | 0.331 | | | | | | | |
| Val | Calculated | 0.346 | 0.092 | 0.149 | 0.176 | 0.125 | 0.111 | | | | | |
| | Found | 0.308 | 0.129 | 0.170 | 0.196 | 0.087 | 0.111 | | | | | |
| Asp | Calculated | 0.151 | 0.208 | 0.207 | 0.248 | 0.186 | | | | | | |
| | Found | 0.120 | 0.182 | 0.277 | 0.251 | 0.171 | | | | | | |
| Gln | Calculated | 0.038 | 0.119 | 0.238 | 0.289 | 0.216 | 0.100 | | | | | |
| | Found | 0.000 | 0.097 | 0.201 | 0.305 | 0.234 | 0.162 | | | | | |
| Phe | Calculated | 0.458 | 0.023 | 0.044 | 0.068 | 0.085 | 0.098 | 0.087 | 0.069 | 0.044 | 0.024 | |
| | Found | 0.495 | 0.065 | 0.047 | 0.052 | 0.068 | 0.069 | 0.070 | 0.060 | 0.039 | 0.036 | |
| Tyr | Calculated | 0.605 | 0.016 | 0.032 | 0.050 | 0.062 | 0.071 | 0.064 | 0.050 | 0.032 | 0.018 | |
| | Found | 0.643 | 0.040 | 0.001 | 0.029 | 0.085 | 0.079 | 0.037 | 0.058 | 0.017 | 0.010 | |
| Trp | Calculated | 0.293 | 0.017 | 0.039 | 0.068 | 0.096 | 0.116 | 0.121 | 0.104 | 0.077 | 0.048 | 0.020 |
| | Found | 0.257 | 0.054 | 0.052 | 0.081 | 0.082 | 0.101 | 0.105 | 0.098 | 0.076 | 0.055 | 0.026 |
| Thr | Calculated | 0.136 | 0.212 | 0.211 | 0.252 | 0.189 | | | | | | |
| | Found | 0.137 | 0.197 | 0.261 | 0.226 | 0.180 | | | | | | |

Figure 6:
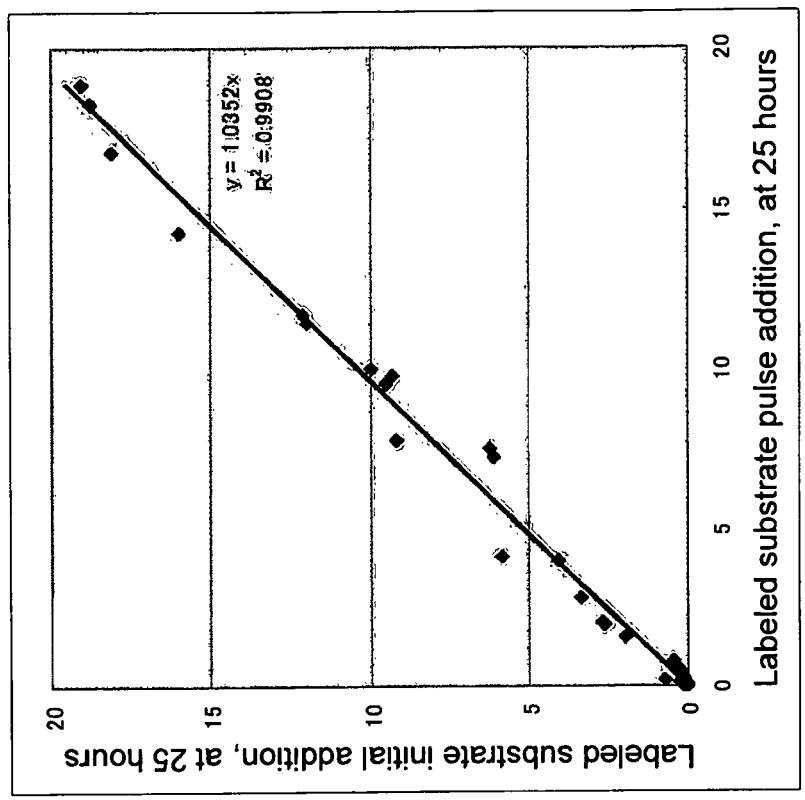
FIG. 6 shows comparison of the analysis results for an isotope-labeled substrate initial addition system and isotope-labeled substrate pulse addition system.
Figure 6:
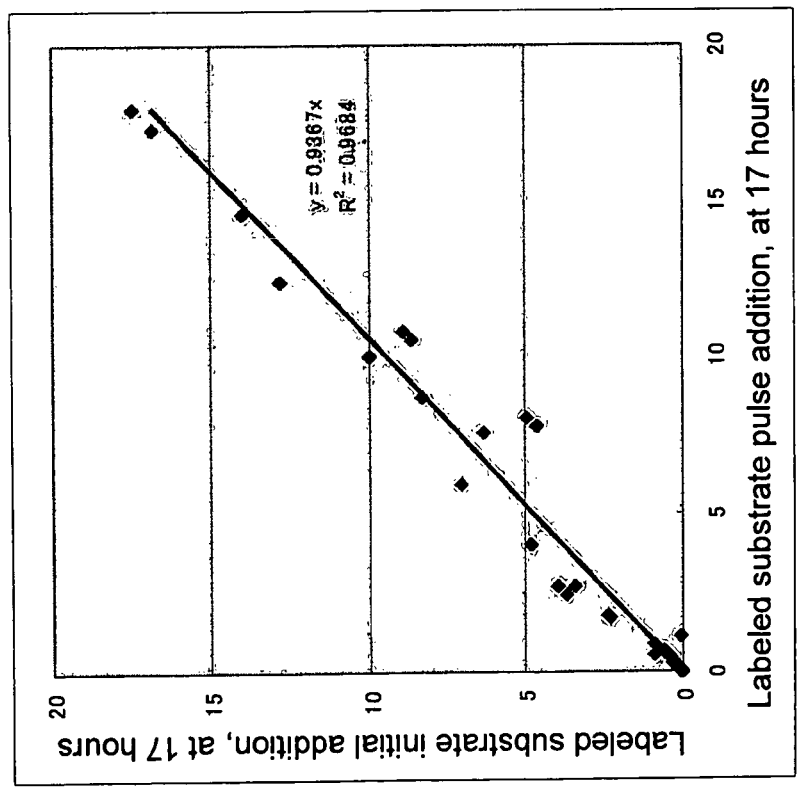

(8) Comparison of Analysis Results of Isotope-Labeled Substrate Initial Addition System and Isotope-Labeled Substrate Pulse Addition System A graph representing the results of comparison of free flux values as results of the analyses of the isotope-labeled substrate initial addition system and isotope-labeled substrate pulse addition system is shown in FIG. 6. The analytical data obtained at 17 hours and 25 hours after the start of cultivation showed good correlation, i.e., represented by correlation coefficients of 0.97 and 0.99, respectively. Therefore, it is considered that results showing the same tendency as that of the results obtained in the isotope-labeled substrate initial addition system were also obtained in the isotope-labeled substrate pulse addition system.

What is claimed is:

1. A method for intracellular metabolic flux analysis comprising the following steps:
    (a) culturing cells in a medium not containing any isotope-labeled substrate to a target phase of the metabolic flux analysis,
    (b) adding an isotope-labeled substrate to the medium and collecting a plurality of cell samples from the isotope-labeled substrate containing medium over a period of time, wherein each cell sample is collected at a distinct and different time point over the period of time,
    (c) measuring isotope distribution of an intracellular metabolite contained in the cells of the plurality of cell samples collected over a period of time, to produce measured data,
    (d) performing a regression analysis for the measured data comprising calculating to calculate an isotope distribution ratio in a steady state, the regression analysis being performed using a specific function represented by equation (I)

$$MDV(Mi)\xi = \{(a*t^\lambda + b)/(d + c*t^\lambda)\}^\eta \quad (I);$$

and
    (e) analyzing a metabolic flux of the cultured cells using the calculated isotope distribution ratio to obtain the analyzed metabolic flux, wherein $MDV(Mi)_\xi$ is a mass distribution vector of a substance $\xi$, $\eta$ is an integer of for larger, $\lambda$ is a positive number, t is time, and a, b, c and d are regression parameters providing a minimum nonlinear regression error.

2. The method according to claim 1, wherein the substrate is added in an amount such that all of the substrate is not consumed during the period of time that samples are collected.

3. The method according to claim 1, wherein the metabolic flux analysis comprises execution of an optimization algorithm.

4. The method according to claim 3, wherein the optimization algorithm is an evolutionary algorithm.

5. The method according to claim 1, wherein the metabolic flux analysis comprises utilizing an intracellular metabolic flux model constructed for an intracellular metabolic flux to be analyzed, and wherein a function representing the intracellular metabolic flux model contains an exchange coefficient of a cell-constituting substance and the same substance in an intracellular pool.

6. The method according to claim 1, wherein the cells are those of a microorganism that produce a compound selected from the group consisting of amino acids, organic acids and nucleic acids.

7. The method according to claim 6, wherein the compound is at least one of an amino acid and an organic acid.

8. The method according to claim 1, wherein culture of the cells is batch culture or fed-batch culture.

9. The method according to claim 1, wherein the intracellular metabolite is at least one of an amino acid and an organic acid, or a major metabolic intermediate thereof, or both.

10. The method according to claim 1, wherein the isotope distribution is measured by mass spectrometry.

11. A method for intracellular metabolic flux analysis comprising:
    (a) adding an isotope-labeled substrate to medium of cells cultured to a target phase of the metabolic flux analysis and collecting cell samples from the isotope-labeled substrate containing medium over a period of time;
    (b) measuring isotope distribution of an intracellular metabolite contained in the cells of the collected cell samples, to produce measured data; and
    (c) performing a regression analysis for the measured data comprising calculating to calculate an isotope distribution ratio in a steady state using a function represented by equation (I)

$$MDV(Mi)\xi = \{(a*t^{\lambda+b})/(d + c*t^\lambda)\}^\eta \quad (I); \text{ and}$$

(d) analyzing a metabolic flux of the cultured cells by using the calculated isotope distribution ratio to obtain the analyzed metabolic flux, wherein $MDV(Mi)_\lambda$ is a mass distribution vector of a substance $\xi$, $\eta$ is an integer of 1 or larger, $\lambda$ is a positive number, t is time, and a, b, c and d are regression parameters providing a minimum non-linear regression error.

* * * * *

UNITED STATES PATENT AND TRADEMARK OFFICE
CERTIFICATE OF CORRECTION

PATENT NO.       : 8,510,054 B2                                  Page 1 of 1
APPLICATION NO.  : 11/048923
DATED            : August 13, 2013
INVENTOR(S)      : Iwatani et al.

It is certified that error appears in the above-identified patent and that said Letters Patent is hereby corrected as shown below:

In the Claims

- Claim 1, Column 23, Line 64 after "integer of" and before "larger"

Please replace "for" with --1 or--

Signed and Sealed this
Fifteenth Day of October, 2013

Teresa Stanek Rea
*Deputy Director of the United States Patent and Trademark Office*